(12) United States Patent
Bonassar et al.

(10) Patent No.: US 10,363,341 B2
(45) Date of Patent: *Jul. 30, 2019

(54) COMPOSITE TISSUE-ENGINEERED INTERVERTEBRAL DISC WITH SELF-ASSEMBLED ANNULAR ALIGNMENT

(71) Applicant: Cornell University, Ithaca, NY (US)

(72) Inventors: Lawrence J. Bonassar, Ithaca, NY (US); Roger Hartl, New York, NY (US); Robert D. Bowles, Ithaca, NY (US); Harry H. Gebhard, Tuebingen (DE)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,406

(22) Filed: Apr. 26, 2017

(65) Prior Publication Data

US 2017/0290953 A1 Oct. 12, 2017

Related U.S. Application Data

(60) Continuation of application No. 14/710,330, filed on May 12, 2015, now Pat. No. 9,662,420, which is a division of application No. 13/319,025, filed as application No. PCT/US2010/033752 on May 5, 2010, now Pat. No. 9,044,335.

(60) Provisional application No. 61/175,680, filed on May 5, 2009.

(51) Int. Cl.
| | |
|---|---|
| A61L 27/44 | (2006.01) |
| A61L 27/36 | (2006.01) |
| A61K 35/32 | (2015.01) |
| A61L 27/20 | (2006.01) |
| A61L 27/24 | (2006.01) |
| A61L 27/38 | (2006.01) |
| A61L 27/52 | (2006.01) |
| A61F 2/44 | (2006.01) |
| A61L 27/22 | (2006.01) |

(52) U.S. Cl.
CPC .......... *A61L 27/3658* (2013.01); *A61F 2/442* (2013.01); *A61K 35/32* (2013.01); *A61L 27/20* (2013.01); *A61L 27/22* (2013.01); *A61L 27/24* (2013.01); *A61L 27/3691* (2013.01); *A61L 27/3817* (2013.01); *A61L 27/3856* (2013.01); *A61L 27/3886* (2013.01); *A61L 27/44* (2013.01); *A61L 27/52* (2013.01); *A61F 2002/444* (2013.01); *A61F 2002/445* (2013.01); *A61F 2002/4435* (2013.01); *A61F 2002/4445* (2013.01); *A61L 2430/38* (2013.01)

(58) Field of Classification Search
None
See application file for complete search history.

(56) References Cited

U.S. PATENT DOCUMENTS

| | | |
|---|---|---|
| 6,340,369 B1 | 1/2002 | Ferree |
| 6,344,058 B1 | 2/2002 | Ferree |
| 6,352,557 B1 | 3/2002 | Ferree |
| 6,419,702 B1 | 7/2002 | Ferree |
| 6,454,804 B1 | 9/2002 | Ferree |
| 6,648,918 B2 | 11/2003 | Ferree |
| 6,648,919 B2 | 11/2003 | Ferree |
| 6,773,713 B2 | 8/2004 | Bonassar et al. |
| 6,997,956 B2 | 2/2006 | Cauthen |
| 7,033,395 B2 | 4/2006 | Cauthen |
| 7,189,235 B2 | 3/2007 | Cauthen |
| 7,537,754 B2 | 5/2009 | Devore et al. |
| 7,556,649 B2 | 7/2009 | Moehlenbruck et al. |
| 7,615,076 B2 | 11/2009 | Cauthen, III et al. |
| 7,651,682 B2 | 1/2010 | Devore et al. |
| 7,651,683 B2 | 1/2010 | Devore et al. |
| 7,670,379 B2 | 3/2010 | Cauthen |
| 8,163,554 B2* | 4/2012 | Kandel ............... A61L 27/3633 435/366 |
| 8,696,750 B2 | 4/2014 | Santerre et al. |
| 9,044,335 B2* | 6/2015 | Bonassar ............ A61L 27/3691 |
| 9,662,420 B2* | 5/2017 | Bonassar ............ A61L 27/3691 |

(Continued)

FOREIGN PATENT DOCUMENTS

| | | |
|---|---|---|
| EP | 1405649 A1 | 4/2004 |
| EP | 1466633 A1 | 10/2004 |

(Continued)

OTHER PUBLICATIONS

Nerurkar et al., "Integrating Theoretical and Experimental Methods for Functional Tissue Engineering of the Annulus Fibrosus," Spine 33(25):2691-2701 (2008).

(Continued)

*Primary Examiner* — Ralph J Gitomer
(74) *Attorney, Agent, or Firm* — Pepper Hamilton LLP

(57) ABSTRACT

The present invention relates to a tissue-engineered intervertebral disc (IVD) suitable for total disc replacement in a mammal and methods of fabrication. The IVD comprises a nucleus pulposus structure comprising a first population of living cells that secrete a hydrophilic protein and an annulus fibrosis structure surrounding and in contact with the nucleus pulposus structure, the annulus fibrosis structure comprising a second population of living cells and type I collagen. The collagen fibrils in the annulus fibrosis structure are circumferentially aligned around the nucleus pulposus region due to cell-mediated contraction in the annulus fibrosis structure. Also disclosed are methods of fabricating tissue-engineered intervertebral discs.

20 Claims, 27 Drawing Sheets

(56) References Cited

U.S. PATENT DOCUMENTS

| | | |
|---|---|---|
| 2002/0007218 A1 | 1/2002 | Cauthen |
| 2002/0082698 A1 | 6/2002 | Parenteau et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0133231 A1 | 9/2002 | Ferree |
| 2002/0151980 A1 | 10/2002 | Cauthen |
| 2002/0151981 A1 | 10/2002 | Ferree |
| 2003/0120345 A1 | 6/2003 | Cauthen |
| 2003/0165473 A1 | 9/2003 | Masuda et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0010251 A1 | 1/2004 | Pitaru et al. |
| 2004/0062753 A1 | 4/2004 | Rezania et al. |
| 2004/0083001 A1 | 4/2004 | Kandel |
| 2004/0193274 A1 | 9/2004 | Trieu |
| 2004/0197367 A1 | 10/2004 | Rezania et al. |
| 2004/0197375 A1 | 10/2004 | Rezania et al. |
| 2005/0002909 A1 | 1/2005 | Moehlenbruck et al. |
| 2005/0112186 A1 | 5/2005 | Devore et al. |
| 2005/0130929 A1 | 6/2005 | Boyd |
| 2005/0149197 A1 | 7/2005 | Cauthen |
| 2006/0062767 A1 | 3/2006 | Phillips |
| 2006/0149380 A1 | 7/2006 | Lotz et al. |
| 2006/0153815 A1 | 7/2006 | Seyda et al. |
| 2006/0160214 A1 | 7/2006 | Masuda et al. |
| 2006/0241773 A1 | 10/2006 | Cauthen |
| 2006/0287731 A1 | 12/2006 | Cauthen, III et al. |
| 2007/0061013 A1 | 3/2007 | Cauthen, III et al. |
| 2007/0073407 A1 | 3/2007 | Cauthen, III et al. |
| 2007/0088438 A1 | 4/2007 | Cauthen, III et al. |
| 2007/0100354 A1 | 5/2007 | Cauthen, III et al. |
| 2007/0150064 A1 | 6/2007 | Ruberte et al. |
| 2007/0156244 A1 | 7/2007 | Cauthen |
| 2007/0156245 A1 | 7/2007 | Cauthen, III et al. |
| 2007/0168041 A1 | 7/2007 | Kadiyala |
| 2007/0218124 A1 | 9/2007 | Devore et al. |
| 2007/0248643 A1 | 10/2007 | Devore et al. |
| 2007/0265626 A1 | 11/2007 | Seme |
| 2008/0045949 A1 | 2/2008 | Hunt et al. |
| 2008/0085292 A1 | 4/2008 | Rezania et al. |
| 2008/0119936 A1 | 5/2008 | Kandel |
| 2008/0195211 A1 | 8/2008 | Lin et al. |
| 2008/0221490 A1 | 9/2008 | Zahos |
| 2008/0249624 A1 | 10/2008 | Josimovic-Alasevic et al. |
| 2009/0030521 A1 | 1/2009 | Lee et al. |
| 2009/0030522 A1 | 1/2009 | Cauthen, III et al. |
| 2009/0035855 A1 | 2/2009 | Ying et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0136576 A1 | 5/2009 | Calvosa et al. |
| 2009/0142311 A1 | 6/2009 | Masuda et al. |
| 2009/0157184 A1 | 6/2009 | Cauthen, III et al. |
| 2009/0196901 A1 | 8/2009 | Guilak et al. |
| 2009/0238806 A1 | 9/2009 | Noh et al. |
| 2010/0021439 A1 | 1/2010 | Moehlenbruck et al. |
| 2010/0179659 A1 | 7/2010 | Li et al. |

FOREIGN PATENT DOCUMENTS

| | | |
|---|---|---|
| WO | 91/16867 A1 | 11/1991 |
| WO | 01/28464 A1 | 4/2001 |
| WO | 01/76654 A1 | 10/2001 |
| WO | 02/00142 A2 | 1/2002 |
| WO | 03/011155 A2 | 2/2003 |
| WO | 03/049669 A2 | 6/2003 |
| WO | 2004/093932 A1 | 11/2004 |
| WO | 2005/055868 A2 | 6/2005 |
| WO | 2005/055877 A2 | 6/2005 |
| WO | 2006/060482 A2 | 6/2006 |
| WO | 2006/068972 A2 | 6/2006 |
| WO | 2006/136905 A2 | 12/2006 |
| WO | 2007/030811 A2 | 3/2007 |
| WO | 2007/134113 A2 | 11/2007 |
| WO | 2008/039530 A2 | 4/2008 |
| WO | 2008/082766 A2 | 7/2008 |
| WO | 2008/098366 A1 | 8/2008 |
| WO | 2008/119023 A2 | 10/2008 |
| WO | 2009/117740 A2 | 9/2009 |

OTHER PUBLICATIONS

Gloria et al., "Dynamic-Mechanical Properties of a Novel Composite Intervertebral Disc Prosthesis," J. Mater. Sci. Mater. Med. 18(11):2159-2165 (2007) (abstract only).

Moss et al., "Nucleus Pulpossus Tissue Repair in Intervertebral Disc Degeneration: Biochemical and Mechanical Evaluation of a Novel Human Disc Cell—Hyaluronan/Elastin Polypeptide Scaffold Composite," Poster No. 1495, 54th Annual Meeting of the Orthopaedic Research Society (Mar. 2008).

Nerurkar et al., "Multi-Scale Tissue Engineering of the Intervertebral Disc," Annual Meeting of the Orthopaedic Research Society (Mar. 2008).

Alini et al., "A Biological Approach to Treating Disc Degeneration: Not for Today, but Maybe for Tomorrow," Eur. Spine J. 11(Suppl. 2):S215-S220 (2002).

Friemark et al., "Cell-Based Regeneration of Intervertebral Disc Defects: Review and Concepts," Int. J. Artif. Organs 32(4):197-203 (2009) (abstract only).

Helen et al., "Three-Dimensional Culture of Annulus Fibrosus Cells within PDLLA/Bioglass Composite Foam Scaffolds: Assessment of Cell Attachment, Proliferation and Extracellular Matrix Production," Biomat. 28(11):2010-2020 (2007) (abstract only).

Wilda et al., "In Vitro Studies of Annulus Fibrosus Disc Cell Attachment, Differentiation and Matrix Production on PDLLA/45S5 Bioglass Composite Films," Biomat. 27(30):5220-5229 (2006) (abstract only).

Mizuno et al., "Biomechanical and Biochemical Characterization of Composite Tissue-Engineered Intervertebral Discs," Biomat. 27(3):362-370 (2006) (abstract only).

Brown et al., "Evaluation of Polymer Scaffolds to be Used in a Composite Injectable System for Intervertebral Disc Tissue Engineering," J. Biomed. Mat. Res. A 74(1):32-39 (2005) (abstract only).

Halloran et al., "An Injectable Cross-Linked Scaffold for Nucleus Pulposus Regeneration," Biomat. 29(4):438-447 (2008) (abstract only).

Kim et al., "The Characterization of PLGA/Small Intestinal Submucosa Composites as Scaffolds for Intervertebral Disc," Key Engineer. Mat. 342-343:389-392 (2007) (abstract only).

Yu et al., "Progress in Scaffold Materials of Intervertebral Disk Tissue Engineering," J. Clin. Rehab. Tissue Engineer. Res. 11(48):9785-9788 (2007) (abstract only).

Hong et al., "(P69) Characterization of PLGA/Demineralized Bone Particle Composites as Scaffolds," Tissue Engineer. A 14(5):820 (2008) (abstract only).

Bowles et al., "Transplantation of Composite tissue Engineered Intervertebral Discs to Maintain Function in the Rat Spine," Presentation, Orthopaedic Research Society Meeting (Mar. 8, 2010).

Bowles et al., "The Role of Annulus Fibrosus Composition on the Mechanical Properties of Tissue Engineered IVD," 56th Annual Meeting of the Orthopaedic Research Society, Poster No. 1306 (2010).

Bowles et al., "Transplantation of Composite Tissue Engineered Intervertebral Discs to Restore Function to the Rat Spine," 56th Annual Meeting of the Orthopaedic Research Society, Poster No. 180 (2010).

Bowles et al., "Self-Assembly of Aligned Tissue-Engineered Annulus Fibrosus and Intervertebral Disc Composite Via Collagen Gel Contraction," Tissue Engineer. A 16(4):1339-1348 (2010).

Mizuno et al., "Tissue-Engineered Composites of Anulus Fibrosus and Nucleus Pulposus for Intervertebral Disc Replacement," Spine 29(12):1290-1298 (2004).

Researchers Create Tissue—Engineered Intervertebral Discs, New York- Presbyterian Neuroscience pp. 6-8 (Fall 2008).

(56) References Cited

OTHER PUBLICATIONS

Seguin et al., "Tissue Engineered Nucleus Pulposus Tissue Formed on a Porous Calcium Polyphosphate Substrate," Spine 29(12):1299-1306 (2004) (abstract only).
Nerurkar et al., "Mechanics of Oriented Electrospun Nanofibrous Scaffolds for Annulus Fibrosus Tissue Engineering," J. Ortho. Res. 25(8):1018-1028 (2007) (abstract only).
PCT/US2010/033752, International Search Report (dated Jul. 1, 2010).
PCT/US2010/033752, International Written Opinion (dated Jul. 1, 2010).
Wan et al., "Biphasic Scaffold for AF Tissue Regeneration," Biomat. 29(6):643-652 (2008).
Chou et al., "Distinct IVD Cell Populations Adopt Similar Phenotypes in 3D Culture," Tissue Engineering Part A 1412:2079-2087 (2008).
Mizuno et al., "Tissue Engineered Composites of Annulus Fibrosus and Nucleus Pulposus for IVD Replacement," Spine 29(12):1290-7 (2004).

\* cited by examiner

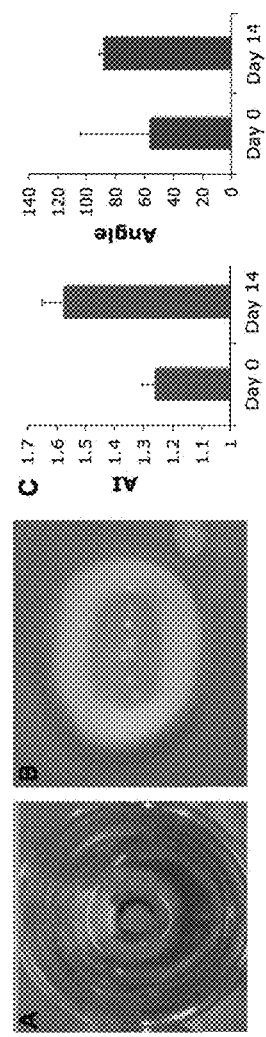
Figures 8A-C

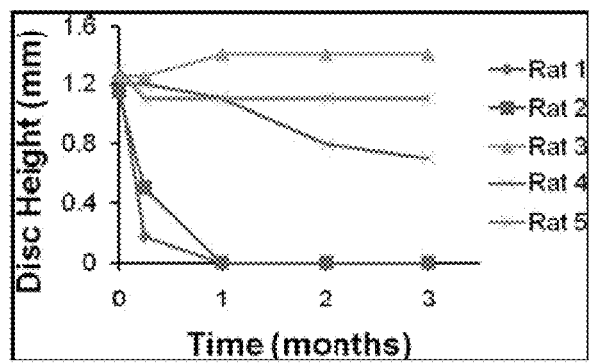
Figure 12
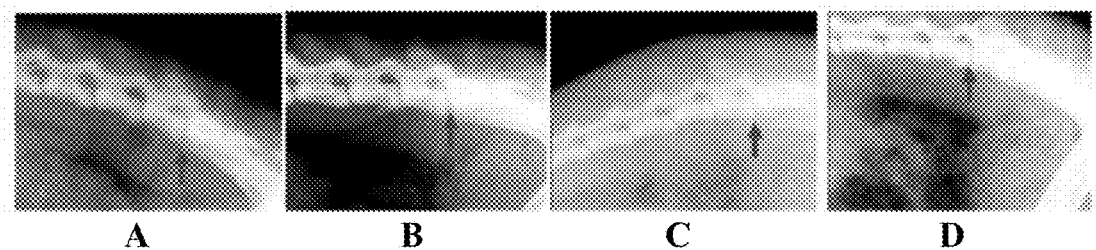
Figures 13A-D
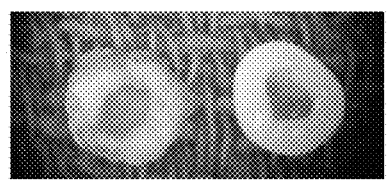
Figure 14

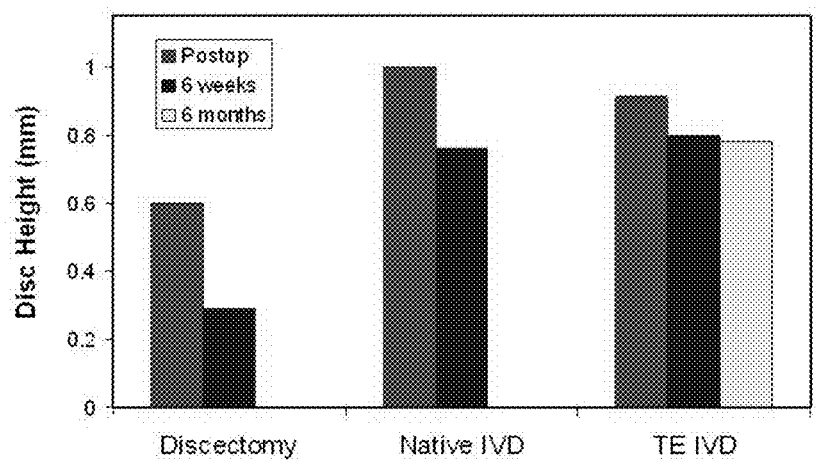
Figure 15
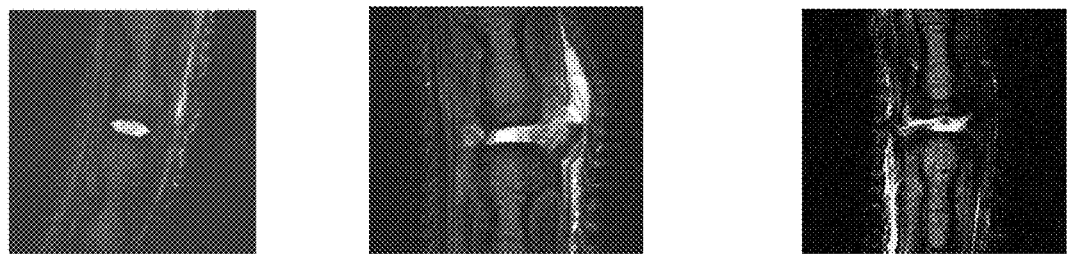
Figures 16A-D

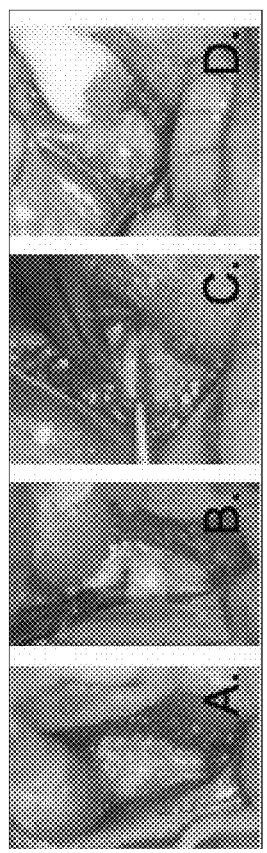
Figures 23A-D

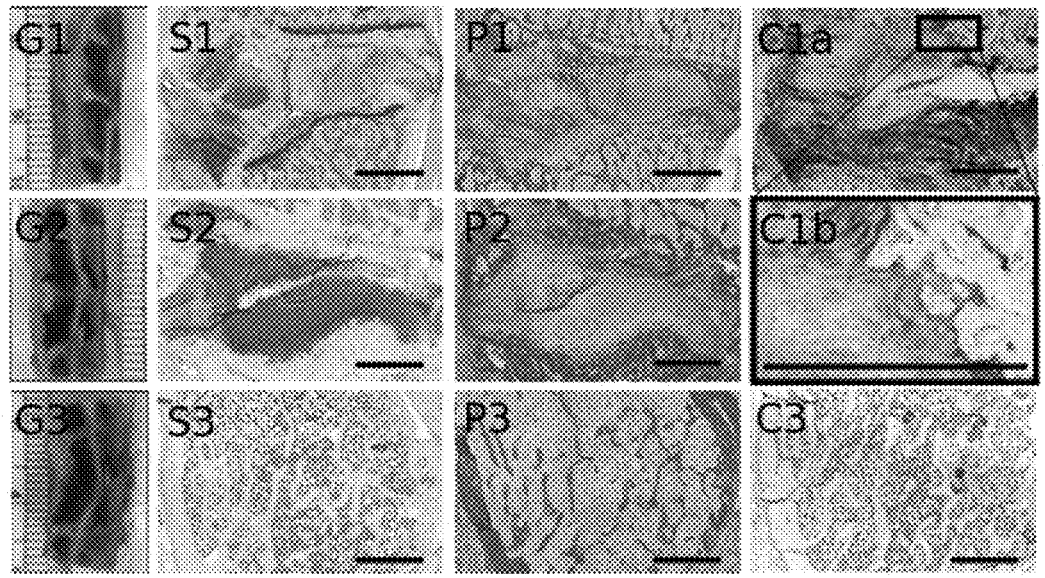
Figure 30
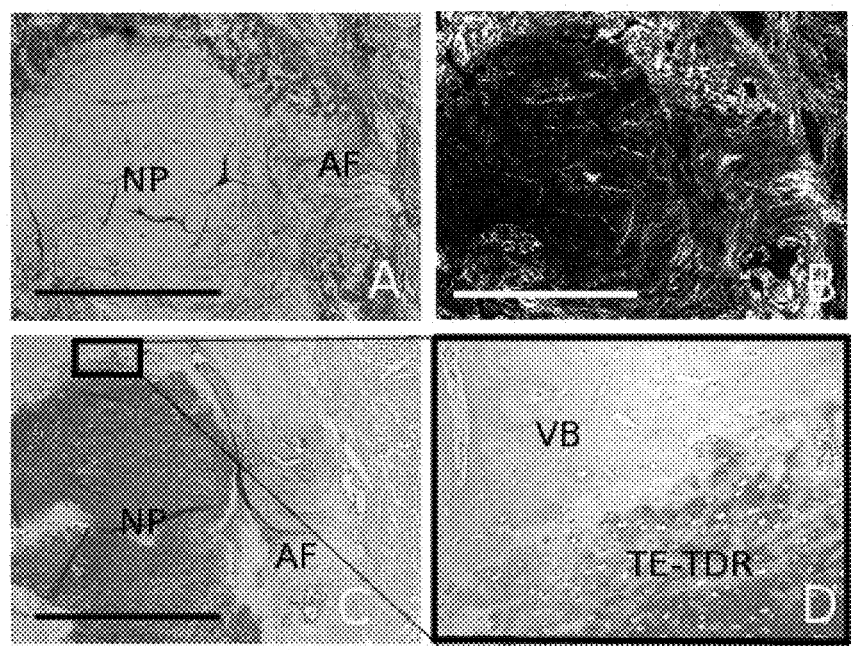
Figures 31A-D

COMPOSITE TISSUE-ENGINEERED INTERVERTEBRAL DISC WITH SELF-ASSEMBLED ANNULAR ALIGNMENT

This application is a continuation of U.S. patent application Ser. No. 14/710,330, filed May 12, 2015, which is a division of U.S. patent application Ser. No. 13/319,025, now U.S. Pat. No. 9,044,335, issued Jun. 2, 2015, which is a national stage application under 35 U.S.C. §371 from PCT Application No. PCT/US2010/033752, filed May 5, 2010, which claims the priority benefit of U.S. Provisional Patent Application Ser. No. 61/175,680, filed May 5, 2009, which are hereby incorporated by reference in their entirety.

This invention was made with Government support under Grant Number DMR 0520404 awarded by NSF. The United States Government has certain rights in the invention.

FIELD OF THE INVENTION

The present invention is directed to tissue-engineered intervertebral discs and methods of their fabrication.

BACKGROUND OF THE INVENTION

Degenerative disc disease ("DDD") is a leading cause of disability in the U.S. and Europe, affecting an estimated 50 million people. As with other musculoskeletal ailments, DDD is a problem that grows as the population ages. Medical options for treatment are limited to analgesic and anti-inflammatory drugs, which do not address underlying causes of the disease. Surgical options for the treatment of DDD are limited to fusion of spinal motion segments and implantation of motion-preserving devices that have limited lifetimes due to material failure and biocompatibility issues. An alternative to these approaches involves regenerating the intervertebral disc ("IVD") using tissue engineering technology. IVD regeneration is particularly challenging, since IVD contains two distinct types of tissue, the annulus fibrosus and nucleus pulposus, that are both important to the mechanical function of the disc.

IVD degeneration is a leading cause of disability in the developed world, with approximately 50% of the population over 50 years old experiencing prolonged back pain (Diwan et al. "Current Concepts in Intervertebral Disc Restoration," *Orthop. Clin. North Am.* 3:453-64 (2000)). Current medical treatment of disc degeneration is purely palliative, focusing on relieving pain, but not restoring function. The primary surgical option for such patients, spinal fusion, alters mechanical loading of remaining IVDs, with pain and adjacent disc degeneration often following (Huang et al, "The Current Status of Lumbar Total Disc Replacement," *Orthop. Clin. North Am.* 35:33-42 (2004)).

As such, significant attention has been paid to developing spinal fusion alternatives, including IVD replacement implants to enable motion between vertebral bodies. Such implants have begun to be used widely in clinical trials and practice including Acroflex (DePuy Acromed), SB Charite III (DePuy Spine), Maverick (Medtronic), and PRODISC® (Spine Solutions, Inc.). While these implants differ in specific design, all share similar components, a combination of metal and plastic parts of similar composition to those used in traditional hip and knee replacements. Although promising, these implants are subject to the failure modes experienced by other synthetic polymer/metal implants including wear, fatigue, and loosening via osteolysis. In fact, these complications are likely to be of even greater concern, given that the environment of the spine may not be able to clear wear debris as efficiently as synovial joints.

An alternative approach to restoring the function of spinal motion segments involves developing biologically based implants using tissue engineering approaches. A properly tissue-engineered IVD tissue implant would restore function and have the ability to continuously remodel in a way similar to native IVD to enable long term function. The great promise of such an approach is tempered by the complexity of the task of creating a tissue with multiple components and complex organization. Most recent efforts in IVD tissue engineering have focused on regenerating individual components of tissue, the annulus fibrosus ("AF") and the nucleus pulposus ("NP").

There have been remarkably few studies examining the function of engineered IVD tissues. The function of the IVD is mechanical, serving to maintain vertebral spacing and enable motion between vertebral segments. Several in vivo studies have demonstrated the ability of cell transplantation techniques to maintain disc height (Meisel et al., "Clinical Experience in Cell-Based Therapeutics: Disc Chondrocyte Transplantation A Treatment for Degenerated or Damaged Intervertebral Disc," *Biomol. Eng.* 24(1):5-21 (2007); Sakai et al., "Immortalization of Human Nucleus Pulposus Cells by a Recombinant SV40 Adenovirus Vector: Establishment of a Novel Cell Line for the Study of Human Nucleus Pulposus Cells," *Spine* 29(14):1515-23 (2004)). For in vitro studies, disc height is not an appropriate measure. Therefore, the best indices of function are the mechanical properties of the tissue, such as the compressive modulus, which is likely related to the ability to maintain height when loaded. Despite the necessity of characterizing such mechanical behavior, only three studies have measured mechanical properties of engineered IVD (Baer et al., "Collagen Gene Expression and Mechanical Properties of Intervertebral Disc Cell-Alginate Cultures," *J. Orthop. Res.* 19(1):2-10 (2001); Séguin et al., "Tissue Engineered Nucleus Pulposus Tissue Formed on a Porous Calcium Polyphosphate Substrate," *Spine* 29(12): 1299-306 (2004); Mizuno et al., "Biomechanical and Biochemical Characterization of Composite Tissue-Engineered Intervertebral Discs," *Biomaterials* 27(3):362-70 (2006)) with the most recent two demonstrating progression of mechanical function with time. Thus, while many cell types and scaffold materials have been investigated, there is no consensus on a method to produce tissue suitable for IVD replacement.

The native IVD has the capacity to regenerate and surgical strategies have been explored that promote healing and repair of an AF defect. Regenerative strategies can be divided into cell therapy, gene therapy, and tissue engineering with scaffolds (Bron et al., "Repair, Regenerative and Supportive Therapies of the Annulus Fibrosus: Achievements and Challenges," *Eur. Spine J.* 18(3):301-13 (2009); Hegewald et al., "Regenerative Treatment Strategies in Spinal Surgery," *Front. Biosci.* 13:1507-1525 (2008)). Implantation of cultured autologous NP and AF cells into the intervertebral disc of animals has been used as an approach for potential future treatment of degenerative disc disease (Okuma et al., "Reinsertion of Stimulated Nucleus Pulposus Cells Retards Intervertebral Disc Degeneration: An In Vitro and In Vivo Experimental Study," *J. Orthop. Res.* 18(6): 988-97 (2000); Gruber et al., "The Sand Rat Model for Disc Degeneration: Radiologic Characterization of Age-Related Changes: Cross-Sectional and Prospective Analyses," *Spine* 27:230-4 (2002)). Others have reported interim results of a human randomized trial using autologous NP cells derived from therapeutic discectomy that were cultured and delivered 12 weeks following discectomy in patients with chronic back pain (Meisel et al., "Clinical Experience in Cell-Based Therapeutics: Disc Chondrocyte Transplantation A Treatment for Degenerated or Damaged Intervertebral Disc," *Biomol. Eng.* 24(1):5-21 (2007)). Their data suggests MR imaging improvement consistent with increased proteoglycan matrix within the NP and a reduction in low back pain at 2 years when compared to controls. It would be unlikely, however, that injection of cells would be effective in cases of more severe disc degeneration. Attempts to use AF cells for regeneration are currently limited due to the problems encountered with isolation and proliferation of these cells in vitro (Bron et al., "Repair, Regenerative and Supportive Therapies of the Annulus Fibrosus: Achievements and Challenges," *Eur. Spine J.* 18(3):301-13 (2009)).

Aligned collagen fibril architectures have been generated by contracting collagen gels under a variety of boundary conditions (Barocas et al., "Engineered Alignment in Media Equivalents: Magnetic Prealignment and Mandrel Compaction," *J. Biomech. Eng.* 120:660-6 (1998); Grinnell and Lamke, "Reorganization of Hydrated Collagen Lattices by Human Skin Fibroblasts," *J. Cell Sci.* 66:51-63 (1984); Thomopoulos et al., "The Development of Structural and Mechanical Anisotropy in Fibroblast Populated Collagen Gels," *J. Biomech. Eng.* 127:742-50 (2005)). One group used this technique to create circumferentially aligned fibrils by imposing an annular outer boundary on contracting collagen gels seeded with human-dermal fibroblasts (Costa et al., "Creating Alignment and Anisotropy in Engineered Heart Tissue: Role of Boundary Conditions in a Model Three-Dimensional Culture System," *Tissue Eng.* 9:567-77 (2003)). The use of an inner mandrel has also been shown to produce aligned structures in tissue-engineered blood vessels (Stegemann et al., "Genetic Modification of Smooth Muscle Cells to Control Phenotype and Function in Vascular Tissue Engineering," *Tissue Eng.* 10:189-99 (2004)). However, none of these methods have been successfully applied to yield a composite IVD with aligned collagen fibrils and AF cells around an engineered NP.

There remains a grand challenge to restore function to the spine by repairing or regenerating IVD tissue. Such an approach is tempered by the complexity of the task of regenerating a tissue with complex organization. The native IVD functions via an intricate load sharing mechanism between its two principle components, the AF and the NP. It is the complex architecture that is responsible for providing mobility to the spine while handling the hoop, torsional, and bending stresses imposed upon it during motion of the spine. However, it is this same complexity that has left a need for an effective treatment for degenerative disc disease.

The present invention overcomes these and other deficiencies in the art.

SUMMARY OF THE INVENTION

One aspect of the present invention relates to a tissue-engineered intervertebral disc suitable for total disc replacement in a mammal. The IVD comprises a nucleus pulposus structure comprising a first population of living cells that secrete a hydrophilic protein and an annulus fibrosis structure surrounding and in contact with the nucleus pulposus structure, the annulus fibrosis structure comprising a second population of living cells and type I collagen. The collagen fibrils in the annulus fibrosis structure are circumferentially aligned around the nucleus pulposus region due to cell-mediated contraction in the annulus fibrosis structure.

Another aspect of the present invention relates to a method of fabricating a tissue-engineered intervertebral disc suitable for total disc replacement in a mammal. This method involves providing a first gel comprising a first population of living cells that secrete a hydrophilic protein; forming the first gel into a predetermined shape and size; providing a second gel comprising a second population of living cells and type I collagen; contacting the formed first gel with the second gel at a region that extends circumferentially around the first gel; and storing the first and second gels under conditions effective for the collagen in the second gel to align circumferentially around the first gel by self-assembly of collagen due to cell-mediated gel contraction in the second gel. The first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

Yet another aspect of the present invention relates to a method of fabricating a tissue-engineered intervertebral disc suitable for total disc replacement in a mammal. This method involves providing a first gel comprising a first population of living cells that secrete a hydrophilic protein; providing a second gel comprising a second population of living cells and type I collagen; forming the second gel around a central mandrel structure; storing the second gel under conditions effective for the collagen in the second gel to align circumferentially around the central mandrel by self-assembly of collagen due to cell-mediated gel contraction in the second gel; and replacing the central mandrel with the first gel. The first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

The present invention provides new techniques to generate composite IVD tissue with an AF structure that more closely mimics the native IVD.

The present invention provides for circumferential fibril alignment in tissue-engineered AF using cell-induced contraction of collagen gels around inner mandrels or nucleus pulposus structures. The directed collagen gel contraction is used to generate circumferentially aligned collagen in the AF portion of the composite implants. Further, additional methods of the present invention relate to an AF composed of concentric lamellae of aligned collagen that are like that of (or mimic) native tissue. These composite tissue-engineered IVD of the present invention with aligned collagen structure have demonstrated remarkable ability to restore function in rats that have undergone lumbar or caudal discectomy.

BRIEF DESCRIPTION OF THE DRAWINGS

FIGS. 3A and 3B are images that show the collagen alignment quantification. FIG. 3A is a second harmonic generation ("SHG") microscopy image. FIG. 3B is a Fourier transform of the image (contrast adjusted). Fourier amplitude components (fast Fourier transform ("FFT") image intensities) were summed up along angles at 5° increments from 0 to 180° and are represented as an arrow and θ. FIG. 3C is a histogram showing the summation of amplitudes of the image intensities along each 5° increment. From this histogram the mode was calculated, and the alignment index ("AI") was calculated according to Equation 1 (infra).

FIG. 5C shows SHG-TPEF images from the inside region during contraction of 1 and 2.5 mg/mL collagen annular constructs over 3 days.

FIGS. 8A-8C are photographs showing composite tissue-engineered IVDs (FIGS. 8A-B), and a graph presenting corresponding SHG alignment data (FIG. 8C). FIG. 8A shows a composite disc before contraction with alginate NP in the center of the well and collagen solution poured around the alginate NP. FIG. 8B shows a composite disc after 2 weeks of culture with collagen gel contracted around alginate NP forming a tissue-engineered composite intervertebral disc according to one embodiment of the present invention. The graph of FIG. 8C shows SHG alignment data measured across the entirety of the contracted collagen gel thickness, indicating a high degree of collagen alignment in the circumferential direction at day 14.

FIG. 9A is a pair of graphs showing the equilibrium compressive modulus (upper graph) and hydraulic permeability (lower graph) of a tissue-engineered IVD according to the present invention. FIG. 9B is a pair of images showing composite tissue-engineered IVDs produced by contracting AF-seeded collagen around an NP seeded core (left photograph). The photograph on the right illustrates a multi-lamellar construct produced by successive contraction of collagen layers, according to one embodiment of the present invention.

FIG. 12 is a graph showing the L5-L6 disc height in animals implanted with a tissue-engineered IVD according to one embodiment of the present invention.

FIGS. 13A-D are x-rays of rat vertebrae immediately post-operative (FIG. 13A), 1 week (FIG. 13B), 1 month (FIG. 13C), and 3 months (FIG. 13D) after receiving a tissue-engineered IVD of the present invention at L5/L6 (arrow). Note maintenance of disc height and absence of deformity.

FIG. 14 is a photograph showing the appearance of native caudal IVD (left) and a tissue-engineered IVD according to one embodiment of the present invention (right).

FIG. 15 is a graph showing CA3-CA4 disc height in controls (Disectomy), animals implanted with a tissue-engineered IVD of the present invention (TE IVD), or their own disc (Native IVD).

FIGS. 16A-D are magnetic resonance images of rat vertebrae: Native disc (FIG. 16A), immediately post-operatively after implantation of TE composite (FIG. 16B), 1 month (FIG. 16C), and 6 months after (FIG. 16D). Note hydration (white), maintenance of disc height, and absence of deformity.

FIGS. 23A-D are photographs showing surgical images of a vertebral column exposed (FIG. 23A), with native disc removed (FIG. 23B), with an engineered disc according to one embodiment of the present invention in the retracted disc space (FIG. 23C), and completed surgery with an engineered disc of the present invention in place (FIG. 23D).

In FIG. 27A, the L4/5 motion segment is exposed. In FIG. 27B, the native disc is removed via scalpel. In FIG. 27C, the vertebral bodies are retracted and the TE-TDR is implanted into the disc space. In FIG. 27D, the vertebral bodies are released, resulting in a successfully implanted TE-TDR specimen.

FIG. 30 shows histology images for three animals. Gross sections (G1-3), Safranin-O (S1-3), and picrosirius red (P1-3) are shown for all three animals. Collagen II IHC shown for animal one (C1a) and three (C3) with magnified vertebral bone implant interface (C1b) are displayed for animal one, as well. G1-2, S1-2, P1-2, and C1a-b show tissue development in discs that maintained disc space. G3, S3, P3, and C3 show fused vertebral bodies at the site of the implanted disc.

FIGS. 31A-D are images showing Picrosirius staining (FIG. 31A) and polarized light showing collagen staining and organization in the AF region of the disc (FIG. 31B). Increased Safranin-O staining in the NP region of the disc is shown in FIG. 31C. Integration between the implanted TE-TDR of the present invention and vertebral body bone is shown in FIG. 31D. (Scale bars=1 mm).

DETAILED DESCRIPTION OF THE INVENTION

Figure 1:
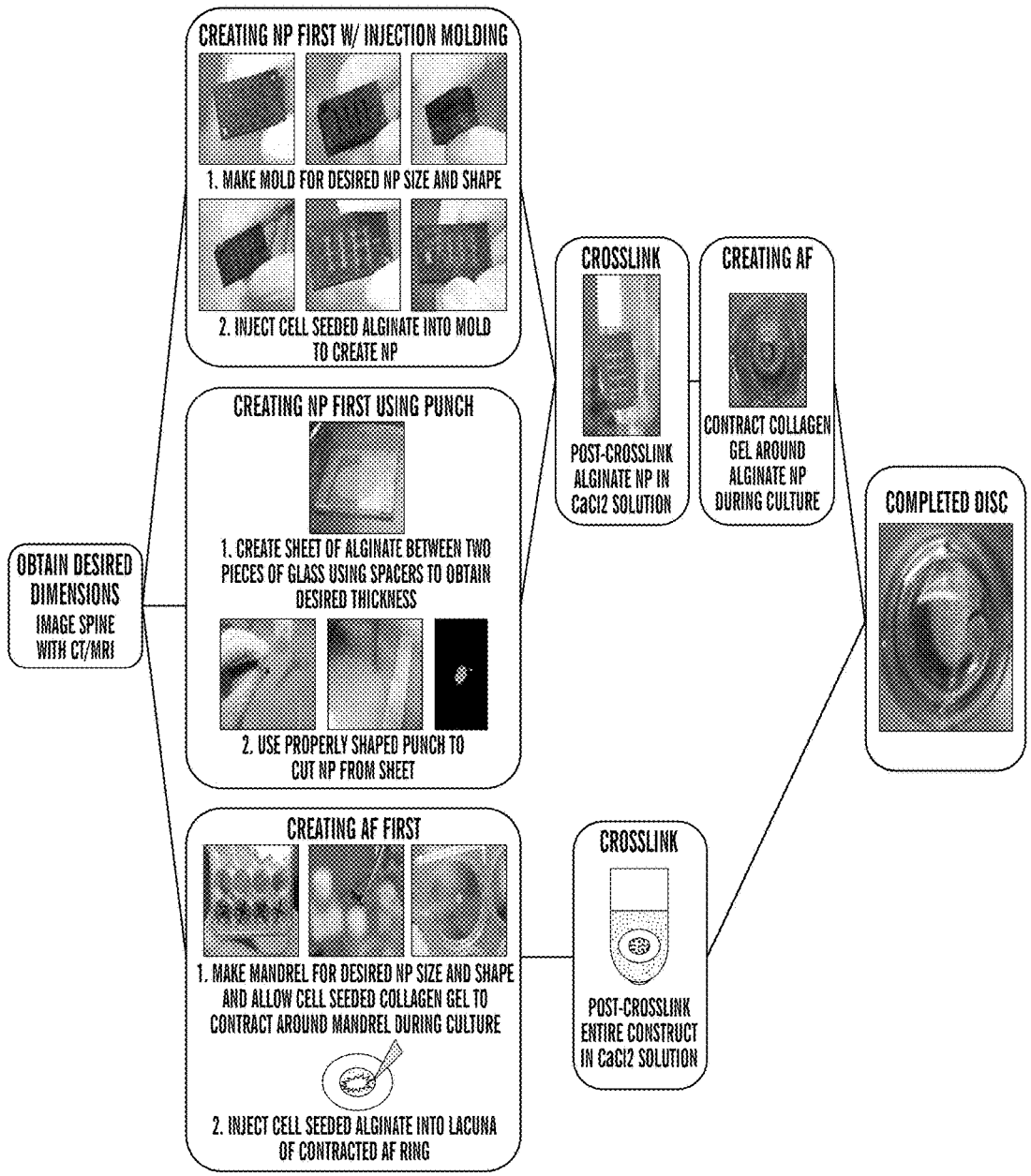
FIG. 1 shows a summary of various embodiments of methods for generating tissue-engineered composite intervertebral discs with aligned collagen in the annulus fibrosus according to the present invention. The desired dimensions for a tissue-engineered IVD are obtained by imaging a spine with CT/MRI. Either the NP structure or the AF structure are first created. The NP structure can be created via injection molding or by creating a sheet of alginate and then cutting out NP structures of a proper shape. When the NP structure is first created, the NP structure is allowed to crosslink and then a collagen gel is contracted around alginate NP during culture to create an AF structure surrounding the NP structure, thereby forming a completed disc. If the AF structure is created first, a mandrel is used and a cell-seeded gel is contracted around the mandrel during culture, after which cell-seeded AF alginate is injected into the lacuna of the contracted AF ring to form the NP. The structure is then crosslinked to form the completed disc.

Intervertebral discs separate the spinal vertebrae from one another and act as natural shock absorbers by cushioning impacts and absorbing the stress and strain transmitted to the spinal column. Intervertebral disc tissues are primarily composed of three regions, the end plates, the annulus fibrosus and the nucleus pulposus. The annulus fibrosus is a tough collagen-fiber composite that has an outer rim of type I collagen fibers surrounding a less dense fibrocartilage and a transitional zone. These collagen fibers are organized as cylindrical layers. In each layer the fibers are parallel to one another; however, the fiber orientation between layers varies between 30 and 60 degrees. This organization provides support during torsional, bending, and compressive stresses on the spine. The end plates, which are found at the upper and lower surfaces of the disc, work in conjunction with the annulus fibrosus to contain the gel-like matrix of the nucleus pulposus within the intervertebral disc. The nucleus pulposus is made up of a soft matrix of proteoglycans and randomly oriented type II collagen fibers in water. The proteoglycan and water content are greatest at the center of the disc and decrease toward the disc periphery. Tissues that effectively mimic these structures can be produced according to the methods described herein.

One aspect of the present invention relates to a tissue-engineered intervertebral disc suitable for total disc replacement in a mammal. The IVD comprises a nucleus pulposus structure comprising a first population of living cells that secrete a hydrophilic protein and an annulus fibrosis structure surrounding and in contact with the nucleus pulposus structure, the annulus fibrosis structure comprising a second population of living cells and type I collagen. The collagen fibrils in the annulus fibrosis structure are circumferentially aligned around the nucleus pulposus region due to cell-mediated contraction in the annulus fibrosis structure.

The nucleus pulposus structure of the tissue-engineered IVD of the present invention includes a first population of living cells. In certain embodiments, the cells of the nucleus pulposus structure (and the annulus fibrosus structure described infra) are seeded into a scaffold, gel, or matrix medium or material. For example, the cells may be present in a gel, such as a hydrogel. The general preparation of hydrogel-cell compositions is known in the art. See, e.g., U.S. Pat. No. 6,773,713 to Bonassar et al., which is hereby incorporated by reference in its entirety. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. Hydrogels can rapidly solidify to keep the cells evenly suspended within a mold (or around or within another solidified gel) until the gel solidifies. Hydrogels can also be biocompatible, e.g., not toxic to cells suspended in the hydrogel. Any suitable hydrogel or other material can be used. Suitable hydrogel examples include, but are not limited to: (1) hydrogels cross-linked by ions, e.g., sodium alginate; (2) temperature dependent hydrogels that solidify or set at body temperature, e.g., PLURONICS™; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™. Examples of materials that can be used to form these different hydrogels include polysaccharides such as alginate, polyphosphazenes, and polyacrylates, which are crosslinked ionically, or block copolymers such as PLURONICS™ (also known as POLOXAMERS™), which are poly(oxyethylene)-poly (oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

A wide range of scaffold or matrix materials have been used as substrates for cell culture and may be suitable for forming the NP (and AF) structure of the tissue-engineered IVDs of the present invention. In general, NP cells have been cultured in hydrogels with alginate (Aguiar et al., "Notochordal Cells Interact With Nucleus Pulposus Cells: Regulation of Proteoglycan Synthesis," *Exp. Cell Res.* 246 (1):129-37 (1999); Baer et al., "Collagen Gene Expression and Mechanical Properties of Intervertebral Disc Cell-Alginate Cultures," *J. Orthop. Res.* 19(1):2-10 (2001); Mizuno et al., "Tissue-Engineered Composites of Anulus Fibrosus and Nucleus Pulposus for Intervertebral Disc Replacement," *Spine* 29(12):1290-7 (2004); Mizuno et al., "Biomechanical and Biochemical Characterization of Composite Tissue-Engineered Intervertebral Discs," *Biomaterials* 27(3):362-70 (2006), which are hereby incorporated by reference in their entirety) and gelatin (Gruber and Hanley, "Biologic Strategies for the Therapy of Intervertebral Disc Degeneration," *Expert Opin. Biol. Ther.* 3(8):1209-14 (2003); Yang et al., "An In-Vitro Study on Regeneration of Human Nucleus Pulposus by Using Gelatin/Chondroitin-6-Sulfate/Hyaluronan Tri-Copolymer Scaffold,"*Artif. Organs* 29(10):806-14 (2005), which are hereby incorporated by reference in their entirety). Both materials are well suited to maintaining NP cell phenotype and enabling proteoglycan synthesis.

In one embodiment of the present invention, the nucleus pulposus structure has cells in an alginate gel. A suitable alginate gel may have about 3% (w/v) alginate. In another embodiment, the alginate gel comprises about 0.5% to about 10% (w/v) alginate. Alternatively, the cells of the nucleus pulposus structure are contained in a gelatin.

The nucleus pulposus structure of the tissue-engineered IVD of the present invention may include type II collagen. Type II collagen serves to provide mechanical support to the tissue and to resist the osmotic swelling pressure exerted by the hydrophilic proteoglycans.

The first population of cells (i.e., cells of the NP structure) may be present in the NP structure at a concentration of about $25 \times 10^6$ cells/ml. In another embodiment, the first population of cells is in a range of concentration of about $1 \times 10^6$ cells/ml to about $50 \times 10^6$ cells/ml.

The first population of cells may include nucleus pulposus cells.

Nucleus pulposus (and/or annulus fibrosis) cells present in the tissue-engineered IVD of the present invention may be isolated from any suitable mammalian source organism, including, without limitation, human, simian, orangutan, monkey, chimpanzee, dog, cat, rat, mouse, horse, cow, pig, and the like. The choice of an animal source for IVD cells is non-trivial, as the time at which the cell population of the NP changes from notochordal to chondrocytic varies with species. Regardless of species chosen, cells are preferably obtained from skeletally mature animals (e.g., murine (Gruber et al., "The Sand Rat Model for Disc Degeneration: Radiologic Characterization of Age-Related Changes: Cross-Sectional and Prospective Analyses," *Spine* 27:230-4 (2002), which is hereby incorporated by reference in its entirety), lapine (Sakai et al., "Immortalization of Human Nucleus Pulposus Cells by a Recombinant SV40 Adenovirus Vector: Establishment of a Novel Cell Line for the Study of Human Nucleus Pulposus Cells," *Spine* 29(14):1515-23 (2004), which is hereby incorporated by reference in its entirety), porcine (Baer et al., "Collagen Gene Expression and Mechanical Properties of Intervertebral Disc Cell-Alginate Cultures," *J. Orthop. Res.* 19(1):2-10 (2001), which is hereby incorporated by reference in its entirety), ovine (Mizuno et al., "Tissue-Engineered Composites of Anulus Fibrosus and Nucleus Pulposus for Intervertebral Disc Replacement," *Spine* 29(12):1290-7 (2004); Mizuno et al., "Biomechanical and Biochemical Characterization of Composite Tissue-Engineered Intervertebral Discs," *Biomaterials* 27(3):362-70 (2006), which is hereby incorporated by reference in its entirety), canine (Aguiar et al., "Notochordal Cells Interact With Nucleus Pulposus Cells: Regulation of Proteoglycan Synthesis," *Exp. Cell Res.* 246(1):129-37 (1999), which is hereby incorporated by reference in its entirety), bovine (Aguiar et al., "Notochordal Cells Interact With Nucleus Pulposus Cells: Regulation of Proteoglycan Synthesis," *Exp. Cell Res.* 246(1):129-37 (1999); Alini et al., "The Potential and Limitations of a Cell-Seeded Collagen/Hyaluronan Scaffold to Engineer an Intervertebral Disc-Like Matrix," *Spine* 28(5):446-54 (2003); Seguin et al., "Tissue Engineered Nucleus Pulposus Tissue Formed on a Porous Calcium Polyphosphate Substrate," *Spine* 29(12): 1299-1306 (2004), which are hereby incorporated by reference in their entirety), simian, and human (Yang et al., "An In-Vitro Study on Regeneration of Human Nucleus Pulposus by Using Gelatin/Chondroitin-6-Sulfate/Hyaluronan Tri-Copolymer Scaffold,"*Artif. Organs* 29(10):806-14 (2005), which is hereby incorporated by reference in its entirety)).

Suitable cells for the tissue-engineered IVD of the present invention may be obtained and/or isolated from essentially any intervertebral disc tissue, such as nucleus pulposus or annulus fibrosus tissues. In one embodiment, cells are obtained from only one type of intervertebral disc source and are not mixed with intervertebral disc cells of another type, e.g., obtained nucleus pulposus cells are essentially free of annulus fibrosus cells. Alternatively, cells can be isolated from bone marrow, adipose, blood, or any other source of mesenchymal stem cells. See, for example, U.S. Pat. Nos. 5,197,985 and 4,642,120, and Wakitani et al., "Mesenchymal Cell-Based Repair of Large, Full-Thickness Defects of Articular Cartilage," *J. Bone Joint Surg. Am.* 76:579-591 (1994), which are hereby incorporated by reference in their entirety.

Intervertebral disc cells can be isolated by any suitable method. Various starting materials and methods for cell isolation are known (see generally, Ian Freshney, CULTURE OF ANIMAL CELLS: A MANUAL OF BASIC TECHNIQUES (5th ed., 1987); Klagsbum, "Large Scale Preparation of Chondrocytes," *Methods Enzymol.* 58:560-564 (1979); Shinmei et al., "The Role of Interleukin-1 on Proteoglycan Metabolism of Rabbit Annulus Fibrosus Cells Cultured In Vitro," *Spine* 13(11): 1284-90 (1988); Maldonado et al., "Initial Characterization of the Metabolism of Intervertebral Disc Cells Encapsulated in Microspheres," *J. Orthop. Res.* 10(5): 677-90 (1992), which are hereby incorporated by reference in their entirety).

Cells can be obtained directly by conventional enzymatic digestion and tissue culture methods, which are described in the Examples (infra). Alternatively, one known method for cell isolation includes differential adhesion to plastic tissue culture vessels. In another method, antibodies that bind to intervertebral disc cell surface markers can be coated on tissue culture plates and then used selectively to bind intervertebral disc cells from a heterogeneous cell population. In yet another method, fluorescence activated cell sorting (FACS) using intervertebral disc-specific antibodies can be used to isolate cells. In still another method, cells can be isolated on the basis of their buoyant density, by centrifugation through a density gradient such as Ficoll. These and other methods are well-known in the art.

It may be desirable in certain circumstances to utilize intervertebral disc stem cells rather than differentiated intervertebral disc cells. Examples of tissues from which stem cells for differentiation, or differentiated cells suitable for transdifferentiation, can be isolated include placenta, umbilical cord, bone marrow, blood, fat, skin, muscle, periosteum, and perichondrium. Cells can be isolated from these tissues through an explant culture and/or enzymatic digestion of surrounding matrix using conventional methods.

In one embodiment of the present invention, cells in the first population of cells secrete the hydrophilic protein proteoglycan. Particular proteins typically found in the extracellular matrix produced by the cells of the NP may also be secreted by cells in the first population of cells. Other hydrophilic proteins may also be secreted in addition to, or alternatively to, proteoglycan. These proteins are characterized by their ability to bind water molecules to provide compressible properties to the nucleus pulposus. Suitable hydrophilic proteins may include one or more of chondroitin sulfate, heparan sulfate, keratan sulfate, and hyaluronic acid.

Many cartilaginous tissues such as IVDs display a heterogeneous collagen microstructure that results in mechanical anisotropy, which is responsible for mechanical function of the tissue to regulate cellular interactions and metabolic responses of cells embedded within these tissues. Using collagen gels seeded with annulus fibrosus cells, constructs of varying structure and heterogeneity may be created to mimic the circumferential alignment of a native IVD. In certain embodiments of the present invention, circumferential alignment may be induced within gels by contracting annular gels around an inner boundary using either, e.g., a polyethylene center or an alginate center to create a composite engineered IVD. This alignment can also be produced according to certain embodiments of the invention in a composite-engineered IVD with, e.g., an alginate nucleus pulposus.

Cells of the first population (and/or any other cells used in the present invention) may be engineered to express a suitable protein, such as a hydrophilic protein. For example, nucleic acid molecules encoding a hydrophilic (or any other) protein can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the protein and a transcription termination (i.e., polyadenylation sequence) can be operably coupled 3' thereof.

Polynucleotides encoding a desired protein can be inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18, or pBR322 may be used. When using insect host cells, appropriate transfer vectors compatible with insect host cells include, pVL1392, pVL1393, pAcGP67, and pAcSecG2T, which incorporate a secretory signal fused to the desired protein, and pAcGHLT and pAcHLT, which contain GST and 6×His tags (BD Biosciences, Franklin Lakes, N.J.). Suitable viral vectors include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of desired protein that is produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible.

The nucleus pulposus structure of the tissue-engineered IVD of the present invention may have an isotropic structure.

In addition to its nucleus pulposus structure, the tissue-engineered IVD of the present invention also includes an annulus fibrosus structure that surrounds the nucleus pulposus structure. Like the nucleus pulposus structure, the annulus fibrosus structure includes a population of living cells, preferably seeded into a gel, matrix, or scaffold, to provide a medium for structure and cell maintenance and growth. The annulus fibrosus structure also contains type I collagen. Collagen fibrils in the annulus fibrosus structure are circumferentially aligned around the nucleus pulposus region as a result of cell-mediated contraction in the annulus fibrosus structure.

Many materials have been used for AF cell culture, and are suitable for use in the tissue-engineered IVD of the present invention. These materials include, without limitation, collagen (both types I and II) (Alini et al., "The Potential and Limitations of a Cell-Seeded Collagen/Hyaluronan Scaffold to Engineer an Intervertebral Disc-Like Matrix," *Spine* 28(5):446-54 (2003); Gruber and Hanley, "Biologic Strategies for the Therapy of Intervertebral Disc Degeneration," *Expert Opin. Biol. Ther.* 3(8):1209-14 (2003); Saad and Spector, "Effects of Collagen Type on the Behavior of Adult Canine Annulus Fibrosus Cells in Collagen-Glycosaminoglycan Scaffolds," *J. Biomed. Mater. Res. A* 71(2):233-41 (2004), which are hereby incorporated by reference in their entirety), PGA (Mizuno et al., "Tissue-Engineered Composites of Anulus Fibrosus and Nucleus Pulposus for Intervertebral Disc Replacement," *Spine* 29(12):1290-7 (2004); Mizuno et al., "Biomechanical and Biochemical Characterization of Composite Tissue-Engineered Intervertebral Discs," *Biomaterials* 27(3):362-70 (2006), which are hereby incorporated by reference in their entirety), small intestine submucosa (Le Visage et al. "Small Intestinal Submucosa as a Potential Bioscaffold for Intervertebral Disc Regeneration," *Spine* 31(21):2423-30 (2006), which is hereby incorporated by reference in its entirety), and chitosan (Dang et al., "Temperature-responsive Hydroxybutyl Chitosan for the Culture of Mesenchymal Stem Cells and Intervertebral Disk Cells," *Biomaterials* 27(3):406-18 (2006), which is hereby incorporated by reference in its entirety).

The second population of cells (i.e., cells of the AF structure) may be present in the AF structure at a concentration of about $0.1$-$5.0 \times 10^7$ cells/ml. In another embodiment the second population of cells is in a range of concentration of about $0.1$-$5.0 \times 10^6$ cells/ml. In another embodiment, the second population of cells is at concentration of about $1 \times 10^6$ cells/ml, $2 \times 10^6$ cells/ml, $3 \times 10^6$ cells/ml, $4 \times 10^6$ cells/ml, or $5 \times 10^6$ cells/ml. The second population of cells may include annulus fibrosus cells.

The annulus fibrosus structure may contain type I collagen at a concentration of about 1 to about 5 mg/ml, at a concentration of about 2.5 to about 5 mg/ml, at a concentration of about 1 to about 30 mg/ml, or at a concentration of about 2.5 to about 30 mg/ml. In a further embodiment, the annulus fibrosus structure comprises type I collagen at a concentration of about 1 mg/ml, about 2 mg/ml, about 2.25 mg/ml, about 2.5 mg/ml, about 3 mg/ml, about 3.5 mg/ml, about 4 mg/ml, about 4.5 mg/ml, or about 5 mg/ml.

The annulus fibrosus structure of the tissue-engineered IVD of the present invention may have an anisotropic structure. Thus, in one embodiment of the present invention, the nucleus pulposus structure has an isotropic structure and the annulus fibrosis structure has an anisotropic structure.

The nucleus pulposus and/or annulus fibrosus structures of the tissue-engineered IVD of the present invention may be permeable to allow nutrient transport to developing tissue. In one embodiment, the composite disc has a hydraulic permeability ranging from about $1 \times 10^{-11}$ m$^2$/Pa s to about $3 \times 10^{-10}$ m$^2$/Pa s. In other embodiments, the hydraulic permeability may range from about $1 \times 10^{-14}$ m$^2$/Pa s to about $1 \times 10^{-9}$ m$^2$/Pa s.

The composite tissue-engineered intervertebral disc of the present invention possesses a unique set of mechanical properties to enable its proper function. In one embodiment, the composite tissue-engineered intervertebral discs have an equilibrium modulus of about 1 to about 6 kPa, an instantaneous modulus of about 5 to about 40 kPa, and a hydraulic permeability of about $1 \times 10^{-11}$ m$^2$/Pa s to about $3 \times 10^{-10}$ m$^2$/Pa s. In other embodiments composite tissue-engineered intervertberal discs have an equilibrium modulus of about 1 to about 500 kPa, an instantaneous modulus of about 5 to about 2000 kPa, and a hydraulic permeability of about $1 \times 10^{-14}$ m$^2$/Pa s to about $1 \times 10^{-9}$ m$^2$/Pa s.

The tissue-engineered IVD of the present invention is suitable for total disc replacement in a mammal. The mammal may be selected from any mammal in need of total IVD replacement. In certain embodiments, the mammal may be in need of total IVD replacement for treatment of or prevention of degenerative disc disease or lower back pain. In other embodiments, the mammal is selected for use in the study of total IVD replacement. In one embodiment, the mammal is selected from a mouse, rat, guinea pig, rabbit, dog, cat, pig, sheep, cow, horse, monkey, or human.

It should be understood that the embodiments discussed with respect to this aspect of the present invention are also contemplated as embodiments relating to other aspects of the invention.

Another aspect of the present invention is a method of fabricating a tissue-engineered intervertebral disc suitable for total disc replacement in a mammal. This method involves providing a first gel comprising a first population of living cells that secrete a hydrophilic protein; forming the first gel into a predetermined shape and size; providing a second gel comprising a second population of living cells and type I collagen; contacting the formed first gel with the second gel at a region that extends circumferentially around the first gel; and storing the first and second gels under conditions effective for the collagen in the second gel to align circumferentially around the first gel by self-assembly of collagen due to cell-mediated gel contraction in the second gel. The first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

FIG. 1 shows a summary of various embodiments of methods for fabricating tissue-engineered composite intervertebral discs with aligned collagen in the annulus fibrosus according to this and other aspects of the present invention. The desired dimensions for a tissue-engineered IVD are obtained by imaging a spine with CT/MRI. Either the NP structure or the AF structure are first created. The NP structure can be created via injection molding or by creating a sheet of alginate and then cutting out NP structures of a proper shape. When the NP structure is first created, the NP structure is allowed to crosslink and then a collagen gel is contracted around alginate NP during culture to create an AF structure surrounding the NP structure, thereby forming a completed disc. If the AF structure is created first, a mandrel is used and a cell-seeded gel is contracted around the mandrel during culture, after which cell-seeded alginate is injected into the lacuna of the contracted AF ring to form the NP. The structure is then crosslinked to form the completed disc.

In one embodiment of the present invention, formation of the second gel is carried out at a temperature of about 37° C. In another embodiment, gel formation is carried out at temperatures ranging from about 20 to about 37° C. In yet another embodiment the second gel is stored for a period of about 3 to about 28 days.

The formation of the first gel (or matrix or scaffold) into a predetermined shape and size is carried out to form a nucleus pulposus structure of an adequate shape and size for implantation into a mammalian vertebrae. In one embodiment of the present invention, the first gel is formed by injection molding techniques, such as those disclosed in U.S. Pat. No. 6,773,713 to Bonassar et al., which is hereby incorporated by reference in its entirety. Alternatively, the gel may be formed by forming the gel into a sheet and cutting out, e.g., circular structures of a suitable size for formation of a nucleus pulposus structure. The thickness of such a sheet may vary depending upon the desired shape and size of the tissue-engineered IVD being formed.

To add to the structural integrity of the IVD structure, the gels may be cross-linked. This technique is taught in U.S. Pat. No. 6,773,713 to Bonassar et al., which is hereby incorporated by reference in its entirety. For example, alginate is an anionic polysaccharide capable of reversible gelation in the presence of an effective concentration of a divalent cation. A hydrogel can be produced by cross-linking the anionic salt of alginic acid, a carbohydrate polymer isolated from seaweed, with ions, such as calcium cations. The strength of the hydrogel increases with either increasing concentrations of calcium ions or alginate. U.S. Pat. No. 4,352,883 (which is hereby incorporated by reference in its entirety) describes the ionic cross-linking of alginate with divalent cations, in water, at room temperature, to form a hydrogel matrix.

In one embodiment of the present invention, the first gel is cross-linked. In a further embodiment of the present invention the first gel is cross-linked in the presence of $CaCl_2$.

The shape and size of the gels (or scaffolds or matrices) according to the present invention can be determined using image-based constructed molds. Using this technique, the mold may reproduce the correct anatomical shape and size for the particular mammal (or patient) to be treated. MRI and μCT have been used for guiding the design of a tissue-engineered meniscus and bone (Ballyns et al., "An Optical Method for Evaluation of Geometric Fidelity for Anatomically Shaped Tissue Engineered Constructs," *Tissue Eng. Part C Methods* (2009); Ballyns et al., "Image-Guided Tissue Engineering of Anatomically Shaped Implants Via MRI and Micro-CT Using Injection Molding," *Tissue Eng. Part A* 14(7):1195-1202 (2008); Cheah et al., "Automatic Algorithm for Generating Complex Polyhedral Scaffold Structures for Tissue Engineering," *Tissue Eng.* 10(3-4):595-610 (2004); Sun et al., "Computer-Aided Tissue Engineering: Application to Biomimetic Modelling and Design of Tissue Scaffolds," *Biotechnol. Appl. Biochem.* 39(Pt 1):49-58 (2004); Van Cleynenbreugel et al., "Trabecular Bone Scaffolding Using a Biomimetic Approach," *J. Mater. Sci. Mater. Med.* 13(12):1245-1249 (2002), which are hereby incorporated by reference in their entirety) and can be employed in designing a tissue-engineered IVD according to the present invention. In other embodiments, the dimensions of the IVD may be altered to enhance the function of the tissue. For example, the thickness of the tissue-engineered composite IVD may be deliberately oversized by a factor of about 1 to about 3 to enable more effective fixation, i.e., a "press fit."

CT and μCT can be used to image the vertebral bodies and provide the outer boundary information of the IVD by examining the surface of the vertebral body (Fields et al., "Role of Trabecular Microarchitecture in Whole-Vertebral Body Biomechanical Behavior," *J. Bone Miner. Res.* 24(9):1523-1530 (2009), which is hereby incorporated by reference in its entirety), as well as provide information on the thickness of the disc space. In addition, a T2 weighted MRI image can be used to provide information on the NP shape and dimensions (Luoma et al., "Disc Height and Signal Intensity of the Nucleus Pulposus on Magnetic Resonance Imaging as Indicators of Lumbar Disc Degeneration," *Spine* 26(6):680-686 (2001), which is hereby incorporated by reference in its entirety). Combining these imaging techniques can produce a model of the native IVD that can be used to create a tissue-engineered IVD of the present invention. Such a technique would be applicable in, e.g., the clinical setting and could produce tissue-engineered IVDs tailored to the particular mammalian patient.

Once the IVD is made, it can be directly implanted, or further cultured, e.g., in vitro, to allow the cells to grow within the hydrogel construct, e.g., for a period of about 1 to 30 days. In one embodiment, in vitro culturing is carried out for about 3 to about 28 days.

The fabrication methods of the present invention may be carried out by using a mandrel or mold in place of the NP gel, around which the AF/collagen solution may be placed under conditions effective for the collagen in the gel to align circumferentially around the central mandrel by self-assembly of collagen due to collagen-mediated gel contraction in the AF/collagen solution. The mandrel or mold may then later be replaced with a formed NP gel.

Thus, another aspect of the present invention is a method of fabricating a tissue-engineered intervertebral disc suitable for total disc replacement in a mammal. This method involves providing a first gel comprising a first population of living cells that secrete a hydrophilic protein; providing a second gel comprising a second population of living cells and type I collagen; forming the second gel around a central mandrel structure; storing the second gel under conditions effective for the collagen in the second gel to align circumferentially around the central mandrel by self-assembly of collagen due to cell-mediated gel contraction in the second gel; and replacing the central mandrel with the first gel. The first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

Implantation of Living Tissue Constructs can be accomplished as taught in U.S. Pat. No. 6,773,713 to Bonassar et al., which is hereby incorporated by reference in its entirety. Generally, to implant a living tissue construct, the implantation site of the mammalian patient can be exposed by surgical resection and the construct implanted directly at that site. Alternatively, if the construct is small enough, the implantation site can be viewed with the aid of, e.g., an endoscope, laparoscope, arthroscope, or esophagoscope, all of which can be modified to include a mechanical articulation and delivery system for implanting the tissue construct through a small incision. During implantation, the site is cleared of bodily fluids including blood, e.g., with a burst of air or suction. Thus, tissue-engineered IVDs of the present invention can be implanted in a mammalian subject.

EXAMPLES

The following examples illustrate various compositions and methods of the invention. The examples are intended to illustrate, but in no way limit, the scope of the invention.

Example 1—Self-Assembly of Aligned Tissue-Engineered Annulus Fibrosus and Intervertebral Disc Composite Via Collagen Gel Contraction Using collagen gels seeded with ovine annulus fibrosus cells, constructs of varying structure and heterogeneity were created to mimic the circumferential alignment of the IVD. Alignment was induced within gels by contracting annular gels around an inner boundary using both a polyethylene center and alginate center to create a composite engineered IVD. Collagen alignment and heterogeneity were measured using second harmonic generation microscopy. Decreasing initial collagen density from 2.5 mg/mL to 1 mg/mL produced greater contraction of constructs, resulting in gels that were 55% and 6.2% of the original area after culture, respectively. As a result, more alignment occurred in annular-shaped 1mg/mL gels compared with 2.5 mg/mL gels ($p<0.05$). This alignment was also produced in a composite-engineered IVD with alginate nucleus pulposus. The resulting collagen alignment could promote further aligned collagen development necessary for the creation of a mechanically functional tissue-engineered IVD.

Example 2—Cell Preparation

The cell preparation techniques were based on previously described techniques (Mizuno et al., "Biomechanical and Biochemical Characterization of Composite Tissue-Engineered Intervertebral Discs," *Biomaterials* 27(3):362-70 (2006), which is hereby incorporated by reference in its entirety). Sixteen IVDs were dissected out of the lumbar spine region of four adult skeletally mature (14 month old) Finn/Dorset cross male sheep (Cornell University Sheep Program, Ithaca, N.Y.) and washed in phosphate-buffered saline ("PBS") (Dulbecco's PBS; Gibco BRL, Grand Island, N.Y.). The AF region of the discs was separated from the NP and dissected into small pieces that were digested in 200 mL of 0.3% w/v collagenase type II (Cappel Worthington Biochemicals, Malvern, Pa.) at 37° C. for 9 h. Digested tissue was filtered through a 100 mm nylon mesh (BD Biosciences, Bedford, Mass.) and centrifuged at 936 g for 7 min. The cells were washed three times in PBS, counted, and seeded at a density of 2500 cells/cm² in culture flasks with Ham's F-12 media (Gibco BRL) containing 10% fetal bovine serum (Gemini Bio Products, Sacramento, Calif.), ascorbic acid (25 μg/mL), penicillin (100 IU/mL), streptomycin (100 μg/mL), and amphotericin B (250 ng/mL). Cells were cultured to confluence at 37° C., 5% $CO_2$ atmosphere, normoxia, pH of 7.2, and 300 mOsm. After culture, cells were removed from T-150 flasks with 0.05% trypsin (Gibco). Cell viability and number were counted with a hemocytometer and trypan blue vital dye. Cells were then diluted to the appropriate concentrations and seeded in collagen gels.

Example 3—Collagen Solution Preparation and Collagen Construct Fabrication

Collagen type I was obtained from rat tails using established protocols (Pel-Freez Biologicals, Rogers, Ariz.) (Elsdale and Bard, "Collagen Substrata for Studies on Cell Behavior," *J. Cell Biol.* 54:626-37 (1972), which is hereby incorporated by reference in its entirety). Briefly, tendons were dissected from rat tails and transferred to a solution of dilute acetic acid (0.1%) at a volume of 80 mL/g of tendon at 48° C. for 48 h. The solution was centrifuged at 9000 rpm, and the supernatant was transferred and centrifuged a second time to remove the unsolubilized collagen, blood, and muscle tissue. The solution was then subjected to the bicinchoninic acid assay (Pierce, Rockford, Ill.) to determine the collagen concentration of the resulting solution. The stock solution was stored at 48° C. until needed.

Before producing gels, tissue culture plates were incubated with a 2% bovine serum albumin solution at 37° C. for 1 hour to prevent construct adhesion to tissue culture plates upon gelation. The stock collagen solution was mixed with the appropriate volumes of 1N NaOH, 1×PBS, and 10×PBS to return the pH to 7.0, maintain 300 mOsm, and produce the appropriate collagen concentrations for the study (Saltzman et al., "Three-Dimensional Cell Cultures Mimic Tissues," *Ann. N.Y. Acad. Sci.* 665:259-73 (1992), which is hereby incorporated by reference in its entirety). This solution was immediately mixed at a 1:1 ratio with the cell/media solution and pipetted into the appropriate tissue culture plate and allowed to gel for 30 min at 37° C. After the constructs had gelled, they were floated with 2 mL of the previously described media.

Example 4—Collagen Disc and Annular Constructs

A total of 70 collagen disc constructs were created by pipetting 1 mL of collagen-cell solution into a 24-well tissue culture plate and allowing it to gel. Collagen annular constructs were created by pipetting 1 mL of the collagen-cell solution into a 12-well tissue culture plate with a 1-cm diameter porous polyethylene disc at the center to yield an annular-shaped collagen ring surrounding the polyethylene. The porous disc was selected to encourage gel to remain around the disc when floated with media. Two groups were made for both construct shapes with final collagen concentrations of 2.5 mg/mL and 1 mg/mL and a final cell concentration of $1\times10^6$ cells/mL. The discs were floated with 1 mL of media for the disc constructs and 2 mL of media for annular constructs in each well to maintain a similar degree of floating in the wells during culture. Seven constructs per group were used for the LIVE/DEAD cell viability assay (Invitrogen, Carlsbad, Calif.) immediately after construction. In addition, constructs were cultured for 3 days and allowed to contract freely with 7 constructs per group being harvested at 0, 1, 2, and 3 days. At each time point, constructs were digitally photographed to quantify construct area, and then fixed with phosphate-buffered formalin for 48 h, with sections of each sample being utilized for SHG microscopy analysis of collagen fibril orientation and histology.

Example 5—Composite Discs

Alginate hydrogel NP was produced by mixing 3% (w/v) alginate seeded with $25\times10^6$ cells/mL with 2% $CaSO_4$ at 2:1 ratio and injected between glass plates to produce a 2-mm-thick alginate sheet. A 1.5 mm biopsy punch was shaped into NP shape dimensions obtained from rat lumbar discs and NP was punched out of the sheet. Alginate NP was subsequently placed at the center of a 24-well plate and 0.405 mL of 2 mg/mL collagen solution was pipetted around the alginate NP to produce a 2-mm-thick collagen ring surrounding the 2-mm-thick NP. A total of 21 composite discs were made and 7 constructs were used for the LIVE/DEAD cell viability assay (Invitrogen) immediately after construction. Gels were then floated with 1 mL of media and allowed to culture for 0 and 2 weeks with seven discs being harvested at each time point and processed in a similar manner to annular and disc constructs.

Example 6—Imaging, Microscopy, and Histological Analysis

All constructs were imaged with a digital camera (Canon Powershot G5) and quantitatively analyzed for surface area using the Image J software (NIH, Bethesda, Md.) immediately after harvest on 0, 1, 2, and 3 days.

Figure 2:
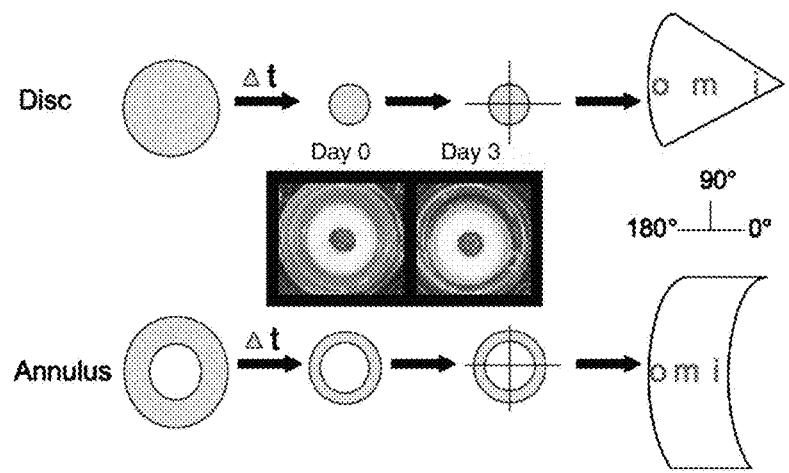
FIG. 2 shows an overview of gel culture and imaging techniques pursuant to various methods of fabricating a tissue-engineered IVD according to the present invention. Disc and annulus were contracted over 3 days before being segmented for imaging. Images were obtained from the outer (o), middle (m), and inner (i) regions of each gel. Coordinates were defined in reference to the imaged gel segments.

Procedures of simultaneous SHG microscopy of collagen type I fibrils and TPEF microscopy of cells were based on those described previously (Zoumi et al., "Imaging Cells and Extracellular Matrix In Vivo By Using Second-Harmonic Generation and Two-Photon Excited Fluorescence," *Proc. Nat'l. Acad. Sci. U.S.A.* 99:11014-9 (2002); Zipfel et al., "Live Tissue Intrinsic Emission Microscopy Using Multiphoton-Excited Native Fluorescence and Second Harmonic Generation," *Proc. Nat'l. Acad. Sci. U.S.A.* 100:7075-80 (2003), which are hereby incorporated by reference in their entirety). SHG and TPEF images were obtained using a custom-built multi-photon microscope with a Ti: Sapphire mode-locked laser providing 100 fs pulses at 80 MHz tuned to a wavelength of 780 nm. Images were acquired using a BioRad (Hercules, Calif.) 1024 laser scanner coupled to an Olympus (Center Valley, Pa.) 1X-70 inverted microscope. Incident light was focused on the sample using either a 40× or a 20× objective. Samples were loaded onto the microscope so that fibrils aligned in the circumferential direction of the constructs were in the 90° direction according to a specified coordinate system (FIG. 2). Two-photon fluorescence and back-propagating second harmonic signals were collected and separated by a dichroic filter into two photomultiplier tubes ("PMTs"). One PMT collected the epi-SHG at 360-410 nm produced by the collagen type I fibrils, and the other PMT collected TPEF signal at 420-500 nm produced by the cells (primarily NADH). For both annular and disc constructs, SHG images were obtained to study the collagen fibril orientation throughout contraction. Z-series were collected with a 20×/0.7 NA water immersion objective to a depth of 80 µm (9 images at 10 µm intervals) at the outer, middle, and inner regions of the gels. The images were obtained for four samples for each time point and construct type. Images were also taken at higher resolution with an Olympus 40×/1.3 NA oil objective to observe fibril and cellular interactions.

Figure 3A:
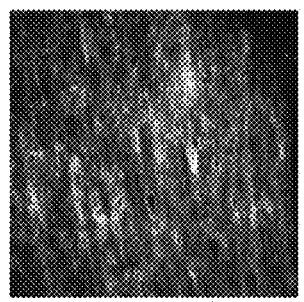
FIGS. 3A-C illustrate collagen alignment in IVDs of the present invention.
Figure 3B:
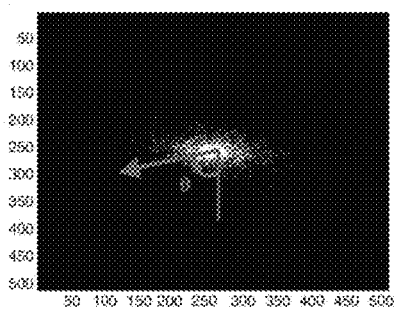
Figure 3C:
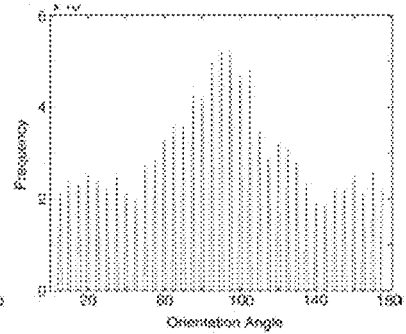

Collagen fibril orientation was calculated from SHG images with a custom MATLAB code based on a previously described technique (Ng et al., "Interstitial Fluid Flow Induces Myofibroblast Differentiation and Collagen Alignment In Vitro," *J. Cell Sci.* 118:4731-9 (2005), which is hereby incorporated by reference in its entirety). This technique has been applied to scanning electron microscopy, and histological and confocal images, and is applied to SHG images here (Chaudhuri et al., "A Fourier Domain Directional Filtering Method For Analysis of Collagen Alignment in Ligaments," *IEEE Trans. Biomed. Eng.* 34:509-18 (1987); Pourdeyhimi et al., "Measuring Fiber Orientation in Nonwovens: 3. Fourier Transform," *Textile Res.* 1 67:143-151(1997); Nishimura and Ansell, "Fast Fourier Transform and Filtered Image Analyses of Fiber Orientation in OSB," *Wood Sci. Technol.* 36:287-307 (2002); van Zuijlen et al., "Morphometry of Dermal Collagen Orientation by Fourier Analysis is Superior to Multi-Observer Assessment," *J. Pathol.* 198:284-91 (2002), which are hereby incorporated by reference in their entirety). The algorithm relies on the fast fourier transform of the SHG images (FIG. 3A). The program summed the intensity of the FFT along lines at 58 increments from 0 to 180° (FIG. 3B) via the coordinate system described (FIG. 2). The angular distribution of summed intensities was calculated, representing the relative orientation of the fibrils within the image (FIG. 3C). From this histogram, the mode was calculated, which represents the angle of maximum alignment, and using Equation 1 an alignment index (AI) was calculated.

$$AI = \frac{\int_{\theta_m - 20°}^{\theta_m + 20°} I \partial\theta}{(40°/180°) \times \int_{0°}^{180°} I \partial\theta} \quad \text{(Equation 1)}$$

AI ranges were from 1 (unaligned) to 4.5 (complete alignment of fibers). Together, the AI provides the degree of alignment observed, whereas the mode angle provides the direction of alignment.

One sample at each time point was fixed for 24 h with 10% phosphate-buffered formalin. The specimens were embedded within paraffin, and serial sections of 5 mm were cut and stained with hematoxylin and eosin for comparison to SHG and TPEF images.

All statistical analysis was performed using three-factor analysis of variance and the Bonferroni post hoc test. The AI parameter was tested for the effect of time in culture (0, 1, 2, and 3 days), region of gel (outside, middle, and inside), and density of gel (1 mg/mL and 2.5 mg/mL).

Example 7—Contraction, Fibril Orientation, and Cellular Orientation Results

Figure 4:
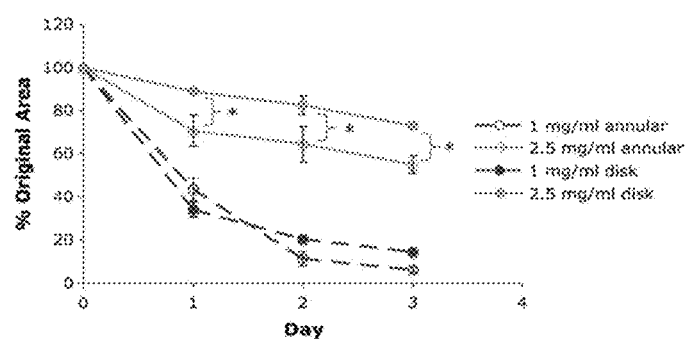
FIG. 4 is a graph showing contraction of cell-seeded gels represented as a percentage of the constructs' original surface area. Data are presented as means±standard deviations for n=7 (*=p<0.05).

On the macro scale, the disc and annular constructs followed a similar contraction profile (FIG. 4). The 2.5 mg/mL discs contracted to 75±2.1% of the original area by day 3 compared with a contraction of 55±4.1% of the original area for the 2.5 mg/mL annular gels on day 3. The 1 mg/mL discs contracted to 15±1.1% of original area, whereas 1 mg/mL annular gels contracted to 6.2±1.4% by day 3. The 1 mg/mL gels contracted very quickly from day 0 to 1 and approached a steady state, compared with the slower and more steady contraction seen in the 2.5 mg/mL gels over the 3 days. Neither the discs nor the annular constructs showed a change in thickness over the 3 days of contraction. In addition, constructs showed no difference ($p<0.05$) between groups in viability after construction with a mean viability of all groups of 92±2%.

Figures 5A, 5B:
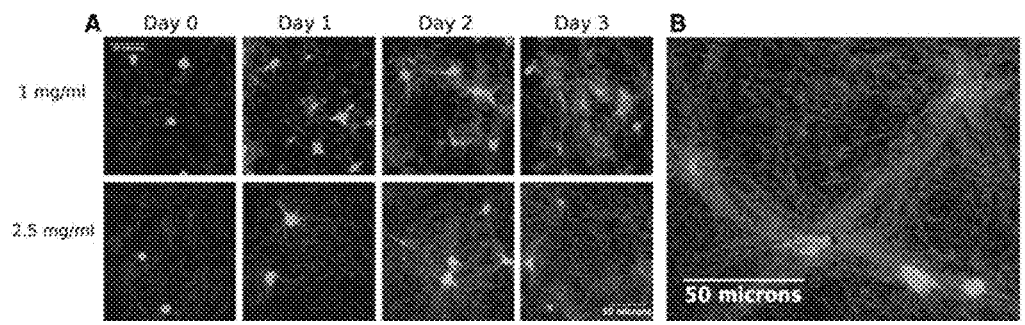
FIGS. 5A-5C are SHG-two-photon excited fluorescence ("TPEF") images from the inside region (FIG. 5A) during contraction of 1 and 2.5 mg/mL collagen disc constructs over 3 days, and magnified image (FIG. 5B) showing aligned fibers between cells on day 3 of contraction in 2.5 mg/mL collagen discs.
Figure 5C:
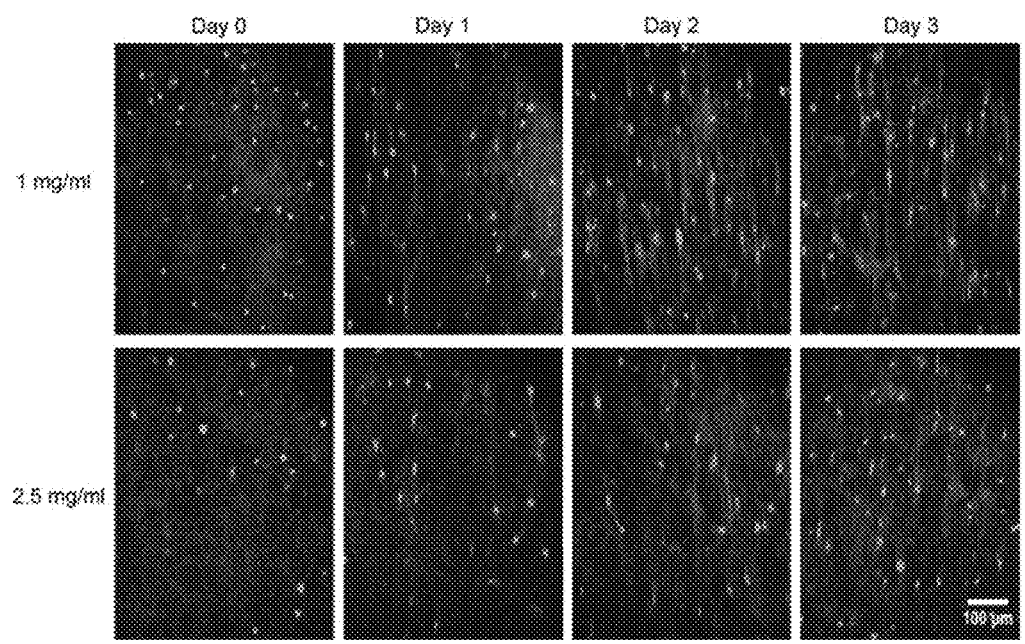

On the micro scale, collagen distribution inside the constructs changed markedly during the contraction process (FIG. 5A). At day 0, collagen was distributed uniformly throughout the sample. Over the course of 3 days, the distribution became more heterogeneous in the discs, with more collagen evident in the pericellular region surrounding AF cells. This effect occurred at both concentrations, but was more pronounced in 1.0 mg/mL gels. Further, in regions where cells were in tight proximity, collagen fibers were rearranged to form larger bundles on lines between cells (FIG. 5B). On a larger length scale, this collagen rearrangement resulted in the development of circumferential collagen fibril and cellular alignment within the annular gels (FIG. 5C).

Regarding fibril orientation, collagen discs showed little change in fibril alignment over the 3 days of contraction for both the 1 and 2.5 mg/mL discs, as indicated by AI values that ranged from 1.2 to 1.3 over 3 days. In contrast to the disc constructs, the annular constructs showed a large degree of fibril alignment in all regions of the constructs over the 3 days of contraction (FIGS. 6A-D). The AI of the 1.0 mg/mL annular construct increased from <1.3 at day 0 to 1.6 at day 1, and remained at 1.6 for day 2 and 3. No significant differences were noticed between regions of the constructs on the same day when the data were analyzed based on region.

Figures 6A, 6B, 6C, 6D:
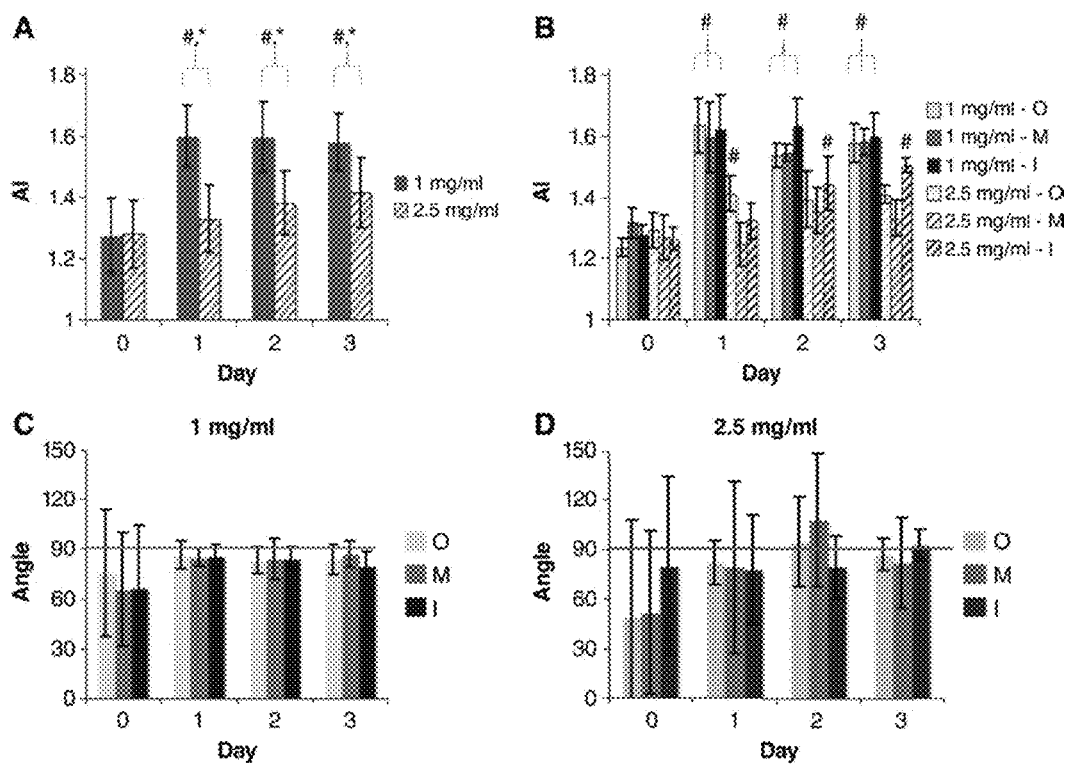
FIGS. 6A-6D are graphs presenting SHG alignment data. The data is shown for collagen annular fibrosus gels with AI broken down by day and gel concentration (n=21) (FIG. 6A); AI further broken down by region of gel (n=7) (O, outside; M, middle; I, inside) (FIG. 6B); and mode angle broken down by day, concentration, and region of gel for 1 mg/mL (n=4) (FIG. 6C); and 2.5 mg/mL gels (n=7) (FIG. 6D). Data are presented as means and standard deviations (#=p<0.05 compared with day 0; *=p<0.05 for indicated groups).

In 2.5 mg/mL gels, AI increased slowly and more steadily over the 3 days of contraction, changing from 1.3 on day 1 to 1.4 by day 3 ($p<0.05$ compared with day 0). In contrast to the 1 mg/mL annular gels, the 2.5 mg/mL gels showed regional heterogeneity, with the middle regions less aligned compared with the inner and outer regions over days 1, 2, and 3 (three-way analysis of variance, $p<0.05$). The 1 mg/mL gels showed significant increases ($p<0.05$) in fibril alignment compared with the 2.5 mg/mL gels at day 1, 2, and 3. With time, mode angles progressed toward 90° and distributions became narrower, indicating a direction of alignment in the circumferential direction (FIGS. 6C and 6D). These trends were present for both 1.0 and 2.5 mg/mL gels, but were more pronounced for 1.0 mg/mL gels. Overall, the data indicate a circumferential alignment of collagen fibrils resulting from annular gel contraction around a polyethylene core.

Figure 7:
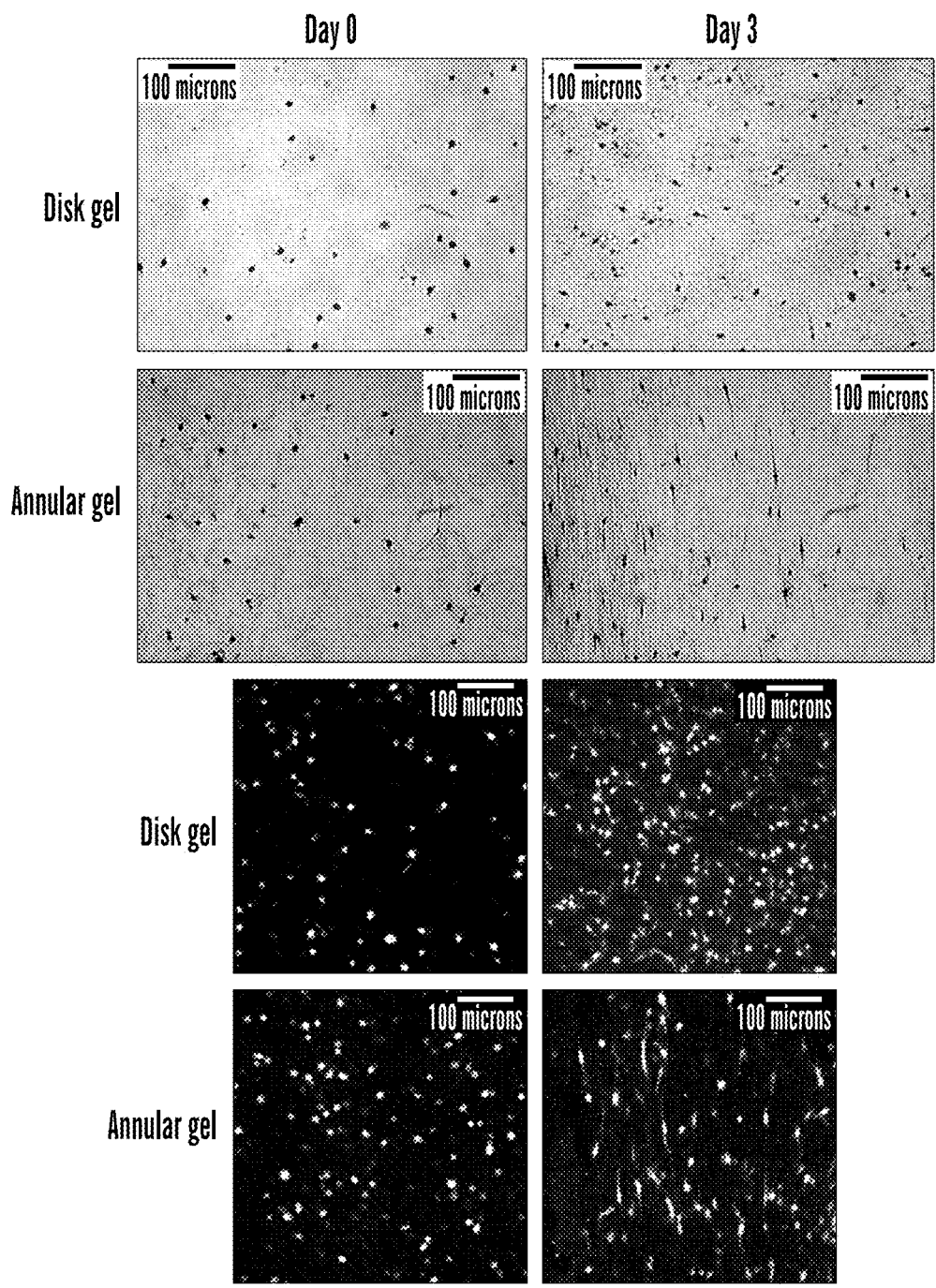
FIG. 7 provides photographs showing hematoxylin and eosin staining and TPEF cellular imaging of 1 mg/mL disc gels and annular gels at day 0 and 3 of contraction from the inside region of the gel.

Regarding cellular orientation, disc gels showed no global alignment of cells over the 3 days of contraction despite showing some evidence of cellular elongation (FIG. 7). However, annular gels showed cellular elongation and circumferential alignment of the cells over the 3 days. The cells developed a spindle-shaped morphology elongated between and parallel to the collagen fibrils similar to the morphology and alignment observed in the native IVD.

Composite discs formed in size and shape of rat lumbar IVD. Collagen gel AF analogue seeded with AF cells contracted around alginate NP analog seeded with NP cells. Collagen fibrils produced an AI of 1.57±0.06 in the circumferential direction (FIGS. 8A-C).

Example 8—Results Show Self-assembly of an Aligned IVD AF Construct from Seeded Collagen Gels for Use in an Engineered IVD Composite The broad goal of this work was to develop a method for self-assembly of an aligned IVD AF construct from seeded collagen gels that can be employed in an engineered IVD composite. This study focuses on remodeling of collagen gels by AF cells and the creation of annular constructs with circumferentially aligned fibrils. Previous efforts to make IVD tissue-engineered constructs have focused mainly on developing the compressive properties of the tissue with less focus on the development of an aligned collagen fibril and cellular architecture in the AF region to provide the necessary tensile and shear properties. Some work has demonstrated the creation of aligned IVD cells in microgrooves (Johnson et al., "Topographical Guidance of Intervertebral Disc Cell Growth In Vitro: Towards the Development of Tissue Repair Strategies for the Anulus Fibrosus," *Eur. Spine J.* 15 Suppl 3:S389-96 (2006), which is hereby incorporated by reference in its entirety) and created tissue-engineered scaffolds with aligned nanoscale fiber orientation for use in AF tissue engineering applications (Nerurkar et al., "Mechanics of Oriented Electrospun Nanofibrous Scaffolds for Annulus Fibrosus Tissue Engineering," *J. Orthop. Res.* 25:1018-26 (2007); Nerurkar et al., "ISSLS Prize Winner: Integrating Theoretical and Experimental Methods for Functional Tissue Engineering of the Annulus Fibrosus," *Spine* 33:2691-701 (2008), which are hereby incorporated by reference in their entirety). However, to date, none of these methods have yielded a composite IVD with aligned collagen fibrils and AF cells around an engineered NP.

In this study, the cellular and fibril architecture were controlled by the boundary conditions imposed on contracting collagen gels. This study demonstrates that over the 3 days of culture, a steady increase of circumferential alignment was observed in both the 2.5 and 1 mg/mL gels (FIG. 7) with a fixed inner boundary. The increased alignment observed in the 1 mg/mL annular gel compared with the 2.5 mg/mL annular gel is likely due to the increased contraction observed in the 1 mg/mL annular gel (6.2±1.4% of original area) compared with the 2.5 mg/mL annular gel (55±4.1% of original area). The increase in alignment was consistent with the profile of the contraction curves of the two concentrations of gels in the annular gels. Further, similar alignment was observed in a composite construct with a circumferentially aligned collagen AF contracted around an alginate NP (FIGS. 8A-C). In contrast to the annular gels and composite, minimal alignment was observed in the disc gels at 3 days. The ability to create an unaligned disc structure in combination with the aligned annular gels may be useful in studying the effects of collagen architecture on tissue development in future studies. Overall, this technique enables control of the degree and heterogeniety of alignment through the original collagen concentrations of the gels and boundary conditions.

Similar techniques have been employed in other tissues to create aligned collagen fibril structures. However, the results of the current study show the ability to use these techniques to create an annular construct with both circumferentially aligned collagen fibrils and aligned AF cells after 3 days of contraction.

Although the main goal of this study was to create collagen alignment in the AF region, it is likely that the cell alignment and shape may be of great importance. To produce a mechanically functional tissue from a collagen gel, long-term culture is likely needed. Fibroblasts are known to increase collagen type I expression when maintained in an aligned spindle shape as compared with a randomly oriented structure and is further enhanced with the application of a tensile stimulation (Lee et al., "Nanofiber Alignment and Direction of Mechanical Strain Affect the ECM Production of Human ACL Fibroblast," *Biomaterials* 26:1261-70 (2005), which is hereby incorporated by reference in its entirety). The spindle-shaped circumferential cellular alignment (FIG. 7) may be advantageous for the future development of the extracellular matrix in long-term culture, as well as for priming AF cells for mechanical stimulation.

The use of SHG-TPEF microscopy enabled the simultaneous study of collagen architecture and cell morphology. More collagen was observed in the pericellular region of the cells in the disc constructs over the 3 days of contraction and was greater in the 1 mg/mL gels than in the 2.5 mg/mL gels. The increased concentration of collagen within these pericellular regions could result from newly synthesized collagen or from pulling of collagen fibrils into the pericellular region by cells. The observed similar profiles of the gel contraction and the development of the increased pericellular collagen between the two concentrations of gels along with the relatively short culture time suggest a contraction mechanism over a collagen production mechanism. The varying collagen architecture demonstrates that although tissue-scale variables, such as total collagen concentration, regulate mechanical properties, it is also important to characterize the microscale collagen architecture that may also yield insight into the process of tissue assembly.

The SHG-TPEF images also showed a cell-fibril-cell interaction. As the gels contracted, fibrils were aligned between adjacent cells in the disc and annular gels (FIG. 5). The alignment of collagen networks between two cellular islands seeded in collagen gels has been proposed in model and experimentally observed by Ohsumi et al., "Three-Dimensional Simulation of Anisotropic Cell-Driven Collagen Gel Compaction," *Biomech. Model Mechanobiol.* 7:53-62 (2007) (which is hereby incorporated by reference in its entirety), but can be seen here in the SHG images occurring between individual cells. This provides a mechanism for the alignment of fibrils observed within the annular gels. Fibrils first become stretched between the cells; as the cells pull and contract around the fixed inner core, the strained fibrils between cells will be predominately oriented in the circumferential direction due to the imposed physical boundary and circumferential tensile stresses. This would not result in aligned fibrils in unbounded discs as no boundaries have been applied and the cells will contract isotropically. Further, these data demonstrate that cell patterning can be employed in collagen gels to further control the resulting collagen architecture of contracted collagen gels.

The fabrication methods of the present invention enable generation of the dominant circumferential alignment of the collagen fibrils/cells in a composite engineered IVD. Further, the ability to deposit successive layers of collagen gels may enable the generation of constructs with multiple lamellae. As a result, contracting collagen gels provide a powerful tool to create the complex structure of the AF.

Example 9—IVD Tissue Engineering

This experiment relates to the development of composite tissue-engineered IVD with both AF and NP regions. In this experiment, the method of which is generally shown in FIG. 1, IVD were harvested from sheep, and the AF and NP separated for isolation of cells from these tissues (Mizuno et al., "Tissue-Engineered Composites of Anulus Fibrosus and Nucleus Pulposus for Intervertebral Disc Replacement," *Spine* 29(12):1290-7 (2004); Mizuno et al., "Biomechanical and Biochemical Characterization of Composite Tissue-Engineered Intervertebral Discs," *Biomaterials* 27(3):362-70 (2006), which are hereby incorporated by reference in their entirety). The AF portion of the IVD was generated from a fibrous PGA mesh shaped either into an anatomic annulus (Mizuno et al., "Tissue-Engineered Composites of Anulus Fibrosus and Nucleus Pulposus for Intervertebral Disc Replacement," *Spine* 29(12):1290-7 (2004), which is hereby incorporated by reference in its entirety) or a right cylindrical annulus (Mizuno et al., "Biomechanical and Biochemical Characterization of Composite Tissue-Engineered Intervertebral Discs," *Biomaterials* 27(3):362-70 (2006), which is hereby incorporated by reference in its entirety). This scaffold was seeded with AF cells, and the center of the construct was filled with NP cells in 2% alginate. Implants were placed into the dorsum of athymic mice for up to 16 weeks. Anatomically shaped discs and the cylindrically shaped discs maintained shape for the duration of implantation, with changes in tissue composition apparent on gross inspection (Mizuno et al., "Biomechanical and Biochemical Characterization of Composite Tissue-Engineered Intervertebral Discs," *Biomaterials* 27(3):362-70 (2006), which is hereby incorporated by reference in its entirety).

Histologic analysis of tissue-engineered IVD samples by Safranin 0 staining revealed that AF and NP tissue in early stage constructs appeared quite similar (Mizuno et al., "Biomechanical and Biochemical Characterization of Composite Tissue-Engineered Intervertebral Discs," Biomaterials 27(3):362-70 (2006), which is hereby incorporated by reference in its entirety). However, with time, AF tissue began to take on a fibrous appearance, although there was no global organization to the fiber structure, particularly compared to native tissue. In contrast, NP cells were homogenously distributed in the tissue and produced a homogenous matrix that stained heavily for proteoglycans. Analysis of tissue generated by this technique demonstrated that AF and NP tissue contained extracellular matrix components consistent with native IVD phenotype. NP tissue was rich in proteoglycan with very little collagen, while AF tissue had abundant collagen and moderate amounts of proteoglycan (Mizuno et al., "Biomechanical and Biochemical Characterization of Composite Tissue-Engineered Intervertebral Discs," *Biomaterials* 27(3):362-70 (2006), which is hereby incorporated by reference in its entirety). Analysis of collagen by Western blot revealed that the NP portion of the tissue contained predominantly type II collagen, with a small amount of type I, while the AF portion contained predominantly type I, with little to no type II (Mizuno et al., "Tissue-Engineered Composites of Anulus Fibrosus and Nucleus Pulposus for Intervertebral Disc Replacement," *Spine* 29(12):1290-7 (2004), which is hereby incorporated by reference in its entirety).

Figure 9A:
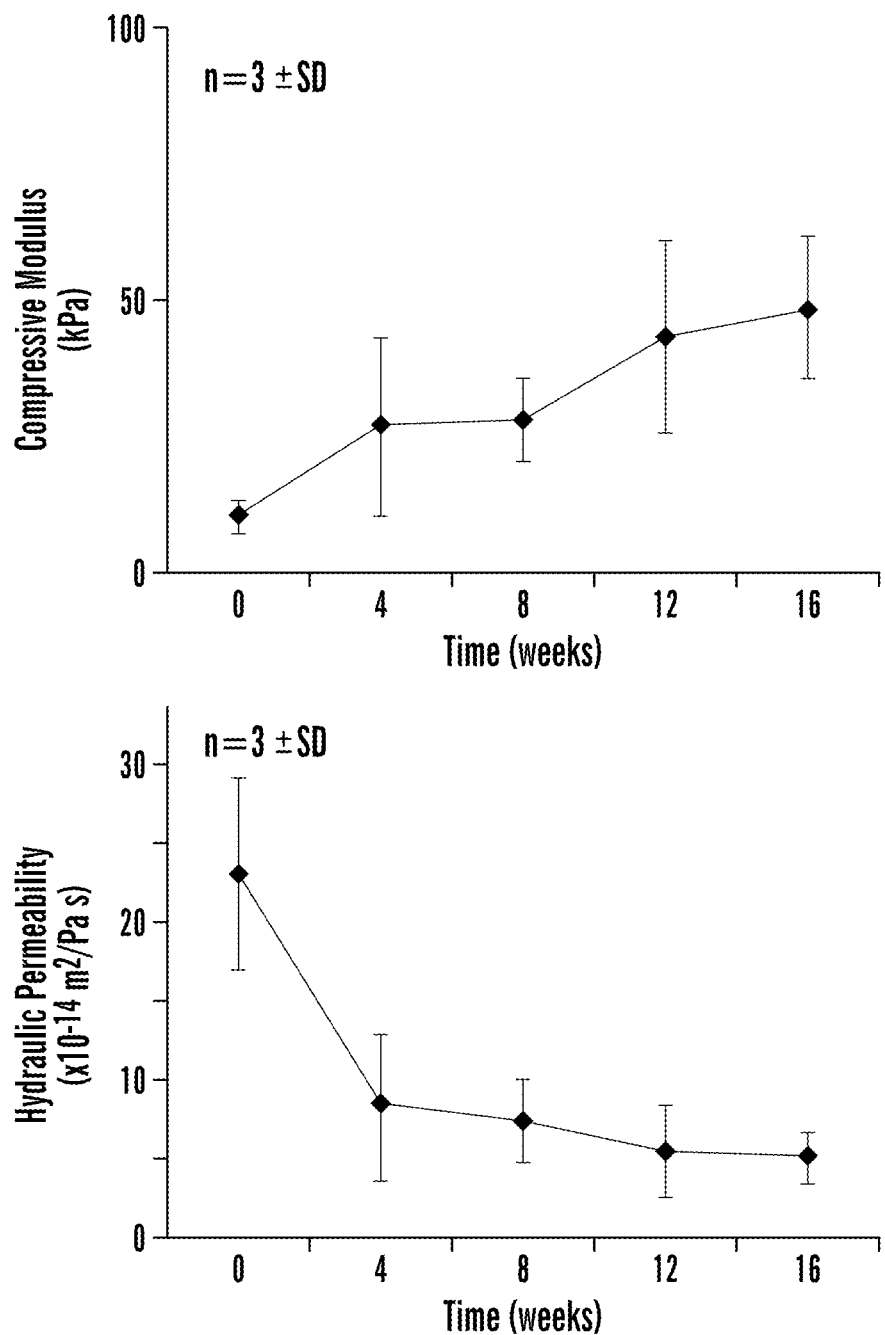
FIGS. 9A-B provide structural data (FIG. 9A) and photographs of tissue-engineered IVDs according to one embodiment of the present invention (FIG. 9B).

The mechanical properties of tissue-engineered IVD was determined using unconfined compression tests. Stress relaxation data was fit to a poroelastic model of material behavior to calculate the equilibrium compressive modulus, which gives a measure of tissue stiffness and the hydraulic permeability, which is related to the ease with which fluid moves through the tissue. Composite tissue-engineered IVD increased 5 fold in compressive modulus to ~50 kPa at 16 weeks as well as decreased 4-fold in hydraulic permeability to ~$5\times10^{-14}$ $m^2$/Pa s (FIG. 9A). At 16 weeks, the compressive modulus was ~30-40% of native intact IVD, (Ho et al., "Spatially Varying Material Properties of the Rat Caudal Intervertebral Disc," *Spine* 31(15):E486-93 (2006), which is hereby incorporated by reference in its entirety) and the hydraulic permeability was ~10-12 fold higher than native IVD (Yao et al., "Effects of Swelling Pressure and Hydraulic Permeability on Dynamic Compressive Behavior of Lumbar Annulus Fibrosus," *Ann. Biomed. Eng.* 30(10):1234-41 (2002), which is hereby incorporated by reference in its entirety). Thus, while there was significant enhancement in mechanical properties, the tissue produced by this method is not comparable in function to native IVD.

As with all materials, the IVD mechanical properties are related to composition and structure. The two main extracellular matrix ("ECM") components of IVD, proteoglycans and collagen, were both found in tissue-engineered IVD in quantities that were typically ~50% of native tissue, while mechanical properties differed by factors of 5-10. This disparity suggests that the organization of IVD ECM may also play a critical role in determining mechanical function. Collagen in native AF is organized into circumferentially aligned lamellae that serve to resist radial expansion during axial loading. While some organization was observed in the AF portion, neither lamellae nor circumferential alignment were observed.

Figure 9B:
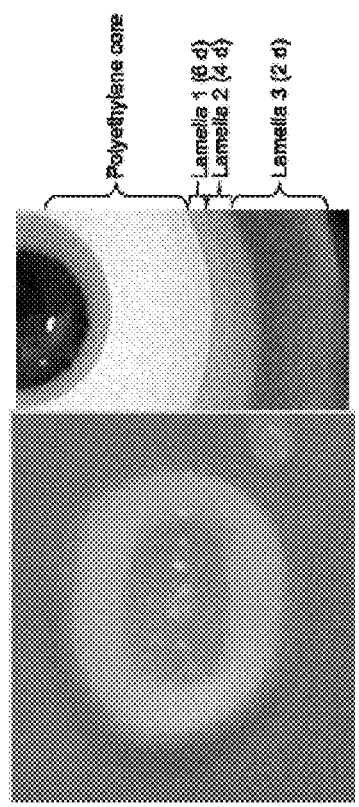
Figure 10:
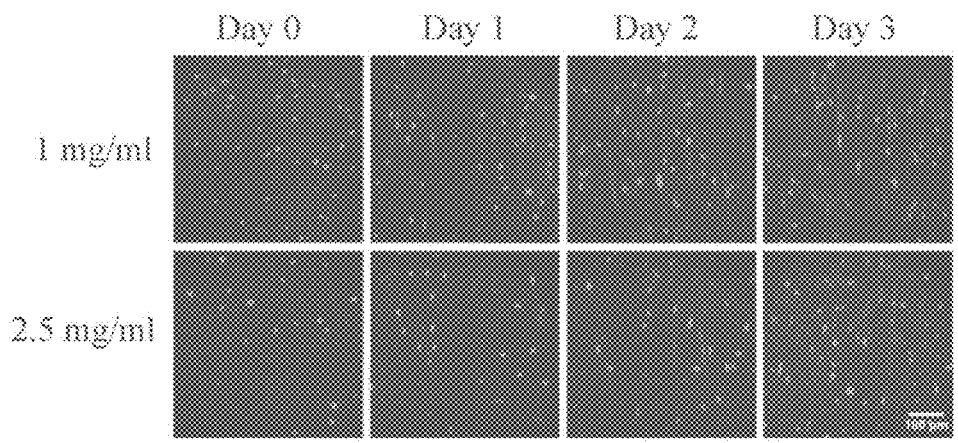
FIG. 10 presents SHG and TPEF images of AF seeded collagen gels. With time, AF cells elongated and collagen aligned parallel to cells.
Figure 11:
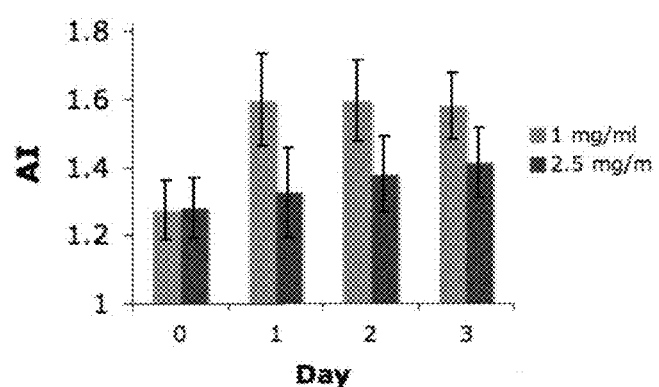
FIG. 11 is a graph illustrating an alignment index of AF-seeded collagen gels showing time- and concentration-dependent organization.

To control collagen alignment in tissue-engineered IVD, the phenomemon of collagen gel contraction was employed (Bell et al., "Production of a Tissue-Like Structure by Contraction of Collagen Lattices by Human Fibroblasts of Different Proliferative Potential In Vitro," *Proc. Nat'l. Acad. Sci. U.S.A.* 76(3):1274-8 (1979), which is hereby incorporated by reference in its entirety). It has been demonstrated that cell-based contraction of gels involves mechanical and biochemical remodeling of collagen, through integrin-mediated traction forces and protease activity (Phillips and Bonassar, "Matrix Metalloproteinase Activity Synergizes With Alpha2beta1 Integrins to Enhance Collagen Remodeling," *Exp. Cell Res.* 310(1):79-87 (2005); Phillips et al., "Fibroblasts Regulate Contractile Force Independent of MMP Activity in 3D-Collagen," *Biochem. Biophys. Res. Commun.* 312(3):725-32 (2003), which are hereby incorporated by reference in their entirety). Further, crosslinking can be used to control the mechanical properties of these gels (Roy et al, "Processing of Type I Collagen Gels Using Non-Enzymatic Glycation," *J. Biomed. Mat. Res. Part A* 93(3):843-51 (2010), which is hereby incorporated by reference in its entirety) and ECM assembly by seeded gels (Roy et al., "Non-Enzymatic Glycation of Chondrocyte-Seeded Collagen Gels for Cartilage Tissue Engineering," *J. Orthop. Res.* 26(11):1434-9 (2008), which is hereby incorporated by reference in its entirety). It has also been demonstrated that local collagen alignment is generated in contracting gels near mechanical boundaries (Costa et al., "Creating Alignment and Anisotropy in Engineered Heart Tissue: Role of Boundary Conditions in a Model Three-Dimensional Culture System," *Tissue Eng.* 9:567-77 (2003), which is hereby incorporated by reference in its entirety). This approach was used to make composite implants with contracted, aligned collagen, and by repeating the contraction procedure multiple times, multi-lamellar constructs were produced (FIG. 9B). Tissue collagen alignment was measured using two photon and second harmonic generation (SHG) microscopy (Bowles et al., "Self-Assembly of Aligned Tissue Engineered Annulus Fibrosus and IVD Composite via Collagen Gel Contraction," *Tissue Eng. Part A.* 16(4):1339-1348 (2010), which is hereby incorporated by reference in its entirety), which enables real time, non-destructive imaging of collagen without histologic stains (Zoumi et al., "Imaging Cells and Extracellular Matrix in Vivo by Using Second-Harmonic Generation and Two-Photon Excited Fluorescence," *Proc. Nat'l. Acad. Sci. U.S.A.* 99(17):11014-9 (2002), which is hereby incorporated by reference in its entirety). Over 3 days, images revealed local alignment of collagen fibrils by AF cells (FIG. 10). Collagen alignment was quantified using custom MATLAB code (Ng et al., "Interstitial Fluid Flow Induces Myofibroblast Differentiation and Collagen Alignment In Vitro," *J. Cell Sci.* 118:4731-9 (2005), which is hereby incorporated by reference in its entirety), which enabled the calculation of an alignment index, defined as the fraction of fibrils aligned within 20° of the mode of the angular intensity distribution. Collagen alignment in gels increased with time in culture (FIG. 11) and was dependent on initial collagen concentration.

Example 10—Implantation of Tissue-Engineered IVD in L5 to L6 Disc Space

To assess the in vivo function of tissue-engineered IVD, samples made by contracting 1 mg/ml collagen gels with $1 \times 10^6$ cells/ml around NP-seeded alginate gels were cultured for 2 weeks and implanted in the L5-L6 space in the spine of athymic rats after discectomy. A total of 6 rats received implants, with 1 animal euthanized at 1 week and 5 at 3 months. Results from this pilot study were very encouraging. Serial x-ray/Faxitron demonstrated that 3 of 5 animals maintained disc height (FIG. 12), with no signs of deformity (FIGS. 13A-D). The remaining 2 animals had collapsed L5-L6 disc space with some focal kyphosis due to a variation in the surgical technique that has since been abandoned. Histology at 1 week showed maintenance of full disc height, new tissue formation in the disc space, and no sign of inflammation or foreign body response. These results demonstrate that this method provides a workable platform for testing the in vivo function of tissue-engineered IVD.

Example 11—Implantation of Tissue-Engineered IVD in CA3-CA4 Disc Space

To assess the in vivo function of tissue-engineered IVD, samples made by contracting 1 mg/ml collagen gels with $1 \times 10^6$ cells/ml around NP-seeded alginate gels were cultured for 2 weeks and implanted into the CA3-CA4 space in the spine of athymic rats after discectomy. Composite discs were generated via contracting collagen around the injection-molded NP core to excellent dimensional tolerance (i.e., to within 7% of the dimensions of the native disc) and greatly resembled the native IVD (FIG. 14).

Using this strategy for fabrication of implants, a total of 12 rats received implants, with 6 animals euthanized at 1 month and 6 months. Results from this pilot study were very encouraging. Serial MRI demonstrated that 12 of 12 animals maintained disc height (FIG. 15), with no signs of deformity (FIGS. 16A-D), and showed 90% hydration. Only the control animals with discectomy had a collapsed CA3-CA4 disc space. Histology at 1 month showed maintenance of 80% disc height, new tissue formation in the disc space, and no sign of inflammation or foreign body response. These results indicate that a workable platform for testing the in vivo function of tissue-engineered IVDs has been developed.

Figure 17:
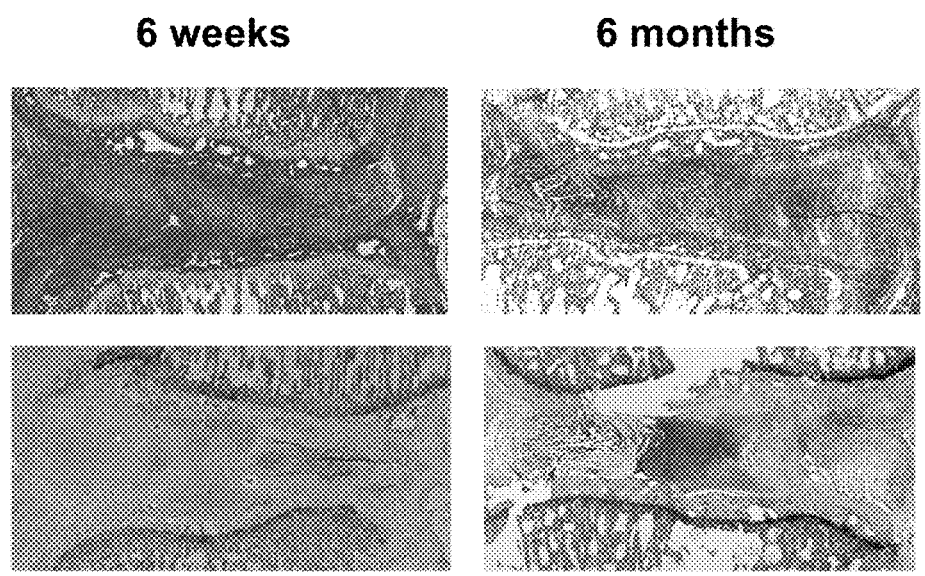
FIG. 17 presents stained images of tissue-engineered IVDs of the present invention at 6 weeks and 6 months in vivo: Picrosirius red (top) and Alcian blue (bottom).

Histological analysis of tissue-engineered IVD implants demonstrated significant tissue development over the course of 6 months as well as excellent integration with the neighboring vertebrae (FIG. 17). Both picosirius red staining (for collagen) and alcian blue staining (for proteoglycans) revealed that no tissue was formed in the disc space after discectomy. In contrast, tissue-engineered IVD showed distinct zonal structure, with the center NP region staining for proteoglycans, while the outer AF region stained heavily for collagen. This effect was observed as early as 6 weeks and was even more pronounced at 6 months. The clefts in the tissue stained with Alcian blue at 6 months are sectioning artifacts, and are not present in the picosirius red sections or other histological samples.

Figure 18:
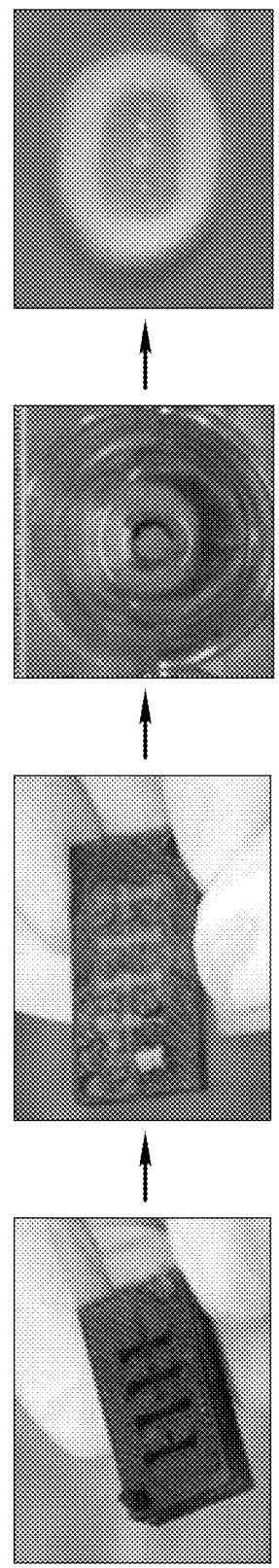
FIG. 18 is a series of photographs illustrating one embodiment of the process of fabricating a composite tissue-engineered IVD of the present invention. According to the illustrated embodiment, an image-based model is used to produce an injectable mold. Cell-seeded alginate NP (3% w/v) was created and placed in the center of a 24 well plate and cell-seeded collagen gel (1 mg/ml) contracted around the NP for 2 weeks.

Example 12—The Role of Annulus Fibrosus Composition on the Mechanical Properties of Tissue-Engineered IVD Composite-engineered IVD discs were created by contracting collagen gels around an alginate NP thus creating circumferentially aligned collagen fibrils in the engineered AF (Nirmalanandhan et al., "Effects of Cell Seeding Density and Collagen Concentration on Contraction Kinetics of Mesenchymal Stem Cell-Seeded Collagen Constructs," *Tissue Eng.* 12(7):1865-72 (2006), which is hereby incorporated by reference in its entirety) (See FIG. 18). Rat lumbar disc dimensions were obtained from µCT images and direct measurements of the rat lumber IVD. Dimensions were then used to create an injection mold of the rat NP. 3% (w/v) alginate seeded with ovine nucleus pulposus cells ($25 \times 10^6$ cells/ml) was injection molded and alginate NP was placed in the center of a 24 well plate. Collagen type I gel solution made from rat tail tendon was made at 3 concentrations (1 mg/ml, 2 mg/ml, and 3.5 mg/ml) and was seeded with ovine annulus fibrosus cells at two seeding densities (1 million cells/ml and 10 million cells/ml) creating six groups. Collagen solution was pipetted around the NP and allowed to gel at 37° C. Constructs were floated with F12 media supplemented with 10% FBS, 100 IU/ml penicillin, 100 µg/ml streptomycin, and 25 µg/ml ascorbic acid. Media was changed every 3 days and constructs cultured for 2 weeks allowing the collagen gel region to contract around alginate NP. Pictures were taken of discs at 0, 6, 12, and 14 days to track contraction of AF region around NP.

At 2 weeks, discs were collected and each group underwent mechanical testing. Mechanical testing was carried out under unconfined compression conditions and strained at 5% increments up to 70% strain. Stress relaxation curves were collected at each strain increment and data was fit to poroelastic model to yield the equilibrium modulus, instantaneous modulus, and hydraulic permeability (Mizuno et al., "Biomechanical and Biochemical Characterization of Composite Tissue-Engineered Intervertebral Discs," *Biomaterials* 27(3):362-70 (2006), which is hereby incorporated by reference in its entirety). Two-way ANOVA with Tukey post-hoc test was performed.

Figure 19:
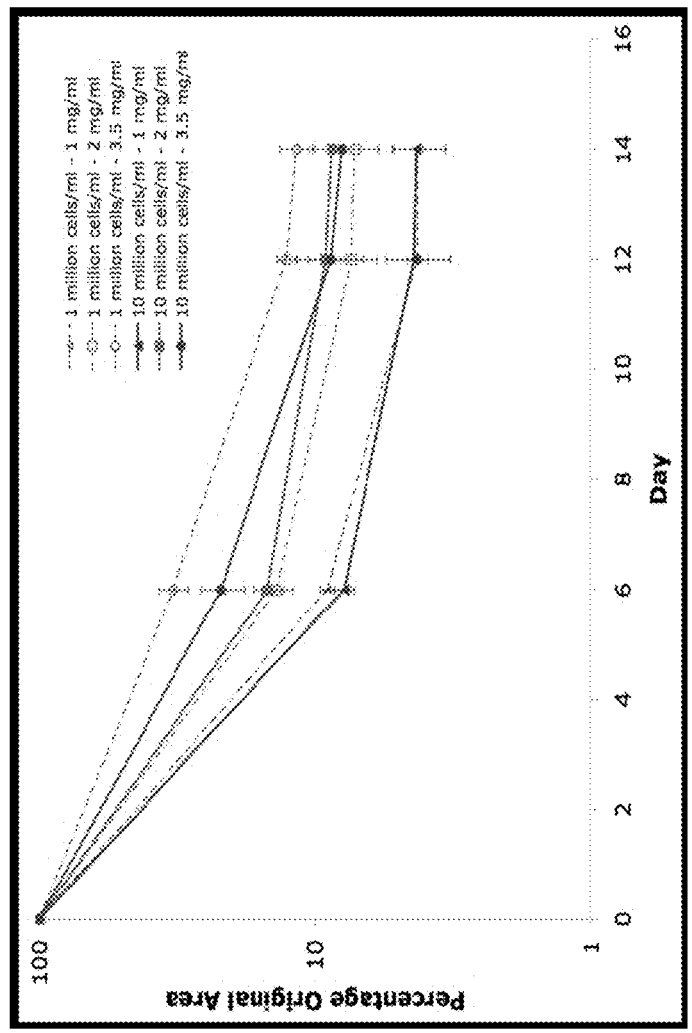
FIG. 19 is a graph showing the contraction of a collagen AF region over 14 days of culture represented as a percentage of original area (n=6, *=p<0.05).

Both seeding density ($p<0.05$) and collagen concentration ($p<0.05$) affected the contraction of the AF portion of composite tissue-engineered IVD (FIG. 19). AF contraction decreased as collagen concentration increased. The effect of cell density was greatest at high collagen concentrations, and was not significant in 1 or 2 mg/ml gels.

Figure 20:
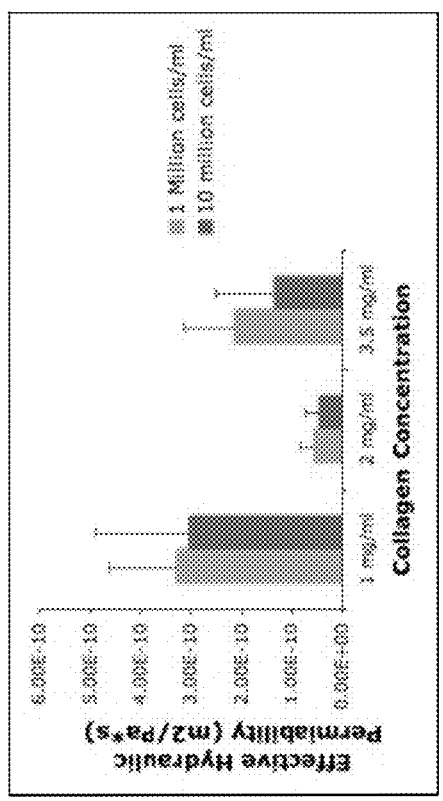
FIG. 20 is a graph showing hydraulic permeability for implants made with two different cell concentrations (1 and 10 million cells/ml) each at three collagen concentrations (1, 2, and 3.5 mg/ml) calculated at 60% strain (n=6,*=p<0.05)
Figure 21A:
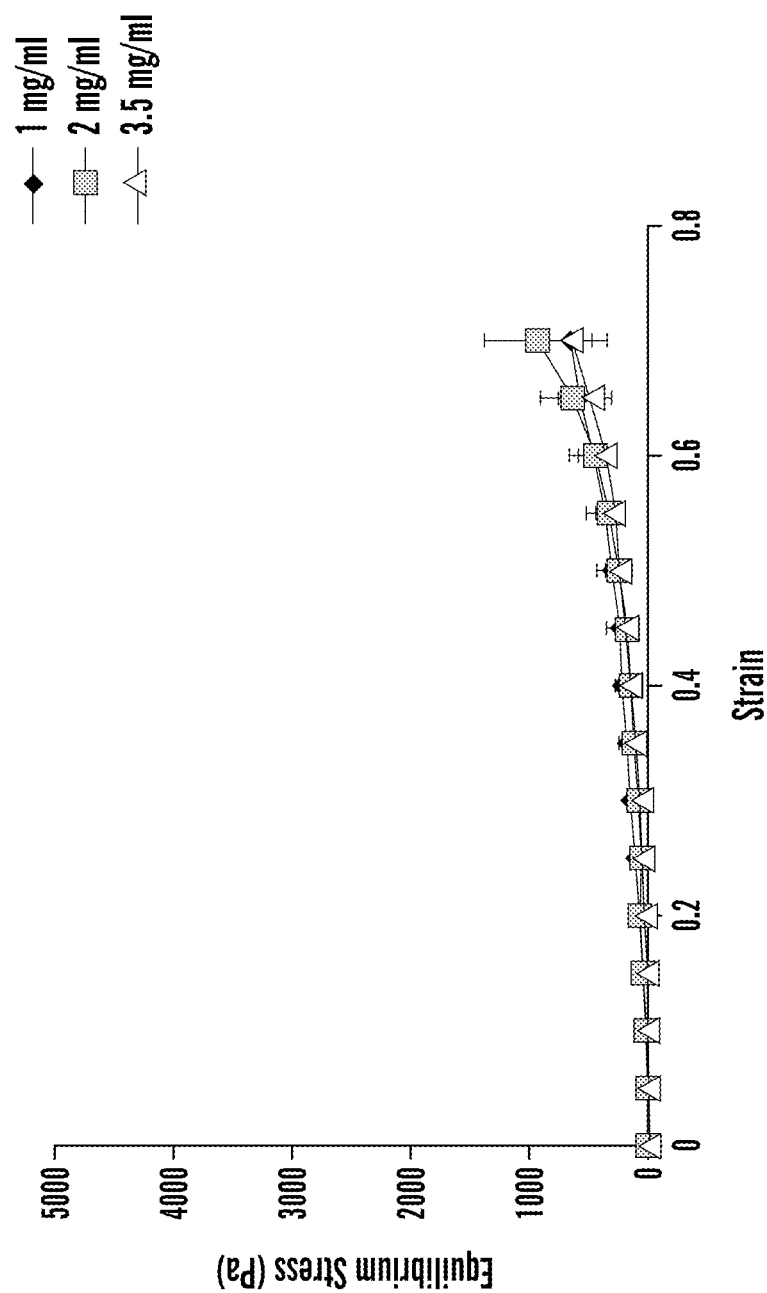
FIGS. 21A-B are graphs showing mean stress strain curves (FIG. 21A, equilibrium and FIG. 21B, instantaneous) for 1 million cells/ml seeded IVDs according to the present invention (n=6, *=p<0.05).
Figure 21B:
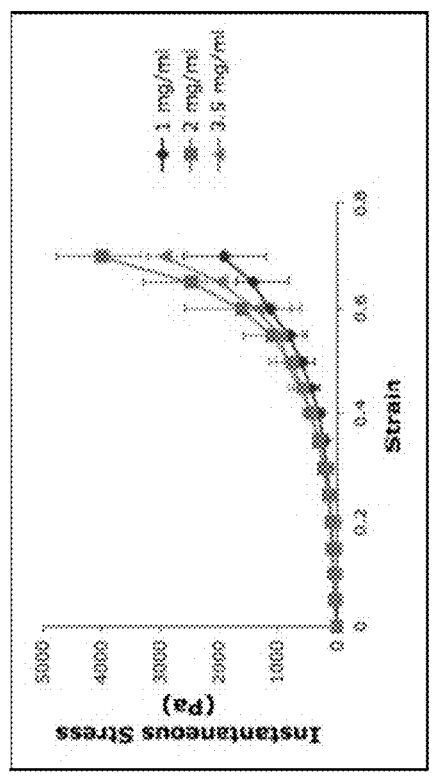
Figure 22A:
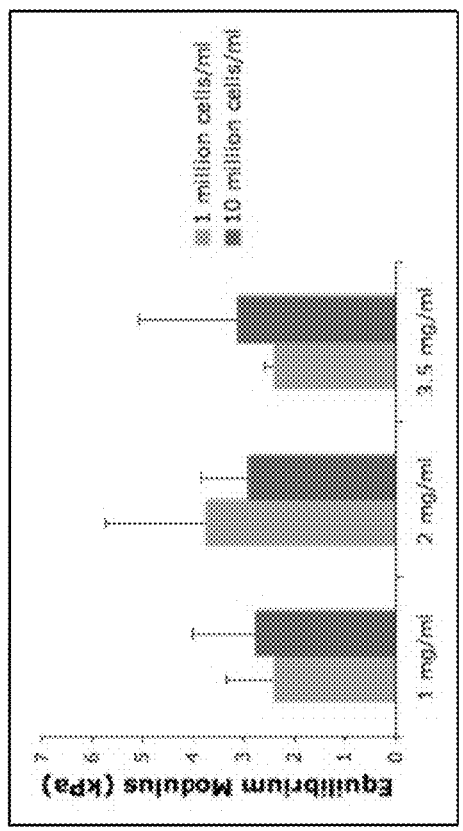
FIGS. 22A-B are bar graphs showing equilibrium (FIG. 22A) and instantaneous (FIG. 22B) modulus at 60% strain (n=6, *=p<0.05).
Figure 22B:
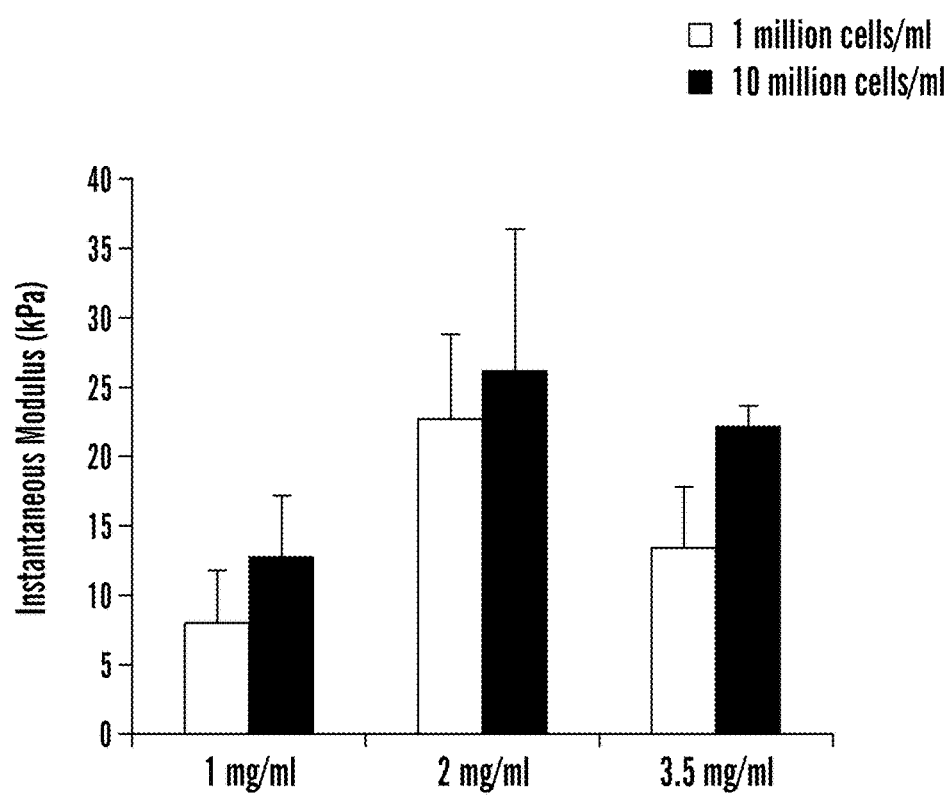

The material property most affected by initial construct composition was the effective hydraulic permeability, which was 10-fold lower in 2 mg/ml gels than 1 mg/ml gels and 3-fold lower in 3.5 mg/ml gels than in 1 mg/ml gels (FIG. 20). The equilibrium stress-strain response was similar for all gel compositions (FIG. 21A); however, the instantaneous stress strain response was significantly higher for 3.5 and 2 mg/ml gels than 1 mg/ml gels at high strains (FIG. 21B). As a result, the equilibrium modulus was not affected by construct composition, while the instantaneous modulus was 2-3 fold higher in 2 and 3.5 mg/ml gels compared to 1 mg/ml gels (FIGS. 22A and 22B).

This study demonstrated the effect of initial cell and collagen concentration on the material properties of composite tissue-engineered IVD. The stiffest and least permeable constructs resulted from constructs with the highest cell and collagen concentrations. The largest changes in mechanical behavior were in the instantaneous modulus and the hydraulic permeability, properties closely related to the ability of the tissue to pressurize during loading. The fact that the instantaneous modulus was 5-10 times higher than the equilibrium modulus suggests that significant pressurization takes place in these samples, as in native IVD. While the effective hydraulic permeability of IVD constructs reported here is significantly higher than native tissue, it is likely that the local permeability of the AF portion of the construct is much lower than that of the composite disc. This is consistent with the idea that the AF portion of the composite is providing the bulk of the resistance in fluid flow in these composites.

The composite mechanical nature of the disc is not observed until 60% strain (FIG. 21B). It is probable that within these discs the high degree of strain is necessary to pressurize the NP within the surrounding AF and allow the composite mechanics to be realized. This is important for the design of tissue-engineered total disc replacements, as it will be necessary for them to be designed in a manor that allows the NP to be pressurized within the AF and not simply placed in the center.

Example 13—Image-Based Tissue Engineering of a Total Intervertebral Disc Replacement for Restoration of Function to the Rat Lumbar Spine It has not been investigated how TE-TDRs will behave in the native disc space. The implanted disc will be subjected to mechanical loading (Sato et al., "In Vivo Intradiscal Pressure Measurement in Healthy Individuals and in Patients With Ongoing Back Problems," *Spine* 24(23):2468-2474 (1999), which is hereby incorporated by reference in its entirety), limited nutrient supply (Bibby et al., "The Pathophysiology of the Intervertebral Disc," *Joint Bone Spine* 68(6):537-542 (2001), which is hereby incorporated by reference in its entirety), and will need to integrate with the native tissue. As a result, a successful TE-TDR will need to be sufficiently stiff to withstand loading in the disc space, sufficiently permeable to allow nutrient transport to the developing tissue, and properly sized to fit into the disc space while sitting flush with the vertebral bodies to facilitate integration. However, currently it is unknown what properties are sufficiently stiff and sufficiently permeable for the successful implant of a TE-TDR into the disc space.

For this reason, the goal of this study was to determine the extent to which a composite collagen/alginate TE-TDR can maintain function of the rat lumbar spine. Specifically, the work produced an image-based collagen/alginate TE-TDR tailored to the L4/L5 disc space of athymic rats and studied the performance of those discs in situ for 4 months. The in vivo performance of composite TE-TDRs was assessed via faxitron x-ray to monitor disc height and histology to characterize the morphology of newly formed tissue and integration of the implant with surrounding tissues.

Magnetic Resonance Imaging data were used in this experiment, and all MRI image data were acquired using a 3.0 Tesla Magnetic Resonance Imaging system (GE Medical Systems, Milwaukee Wis.) equipped with 50 mT/m gradients operating at 150 mT/m/ms. Athymic rats were anesthetized using 3%/2% isoflurane for induction and maintenance, respectively. A sealed poly(methyl 2-methylpropenoate) box with intake and exhaust ports was used for imaging that also contained a warming gel pack to aid in maintaining core body temperature. A Hoult-Deslauriers modular radiofrequency resonator was designed in-house consisting of six inductively coupled, 19 mm diameter resonant loops arranged in a cylindrical geometry of length 35 mm with an inductively coupled drive loop placed at one end.

A 2D axial $T_2$-weighted fast spin echo ("SE") sequence was used to visualize the NP region within the disc. Acquisition parameters included a 90 ms echo time, a 5500 ms repetition time and a 16-length echo train using an 8.0 cm×6.4 cm field of view. A 320×256 matrix was reconstructed to 512×512 providing 0.16 mm×0.16 mm×1.0 mm resolution.

Figure 26:
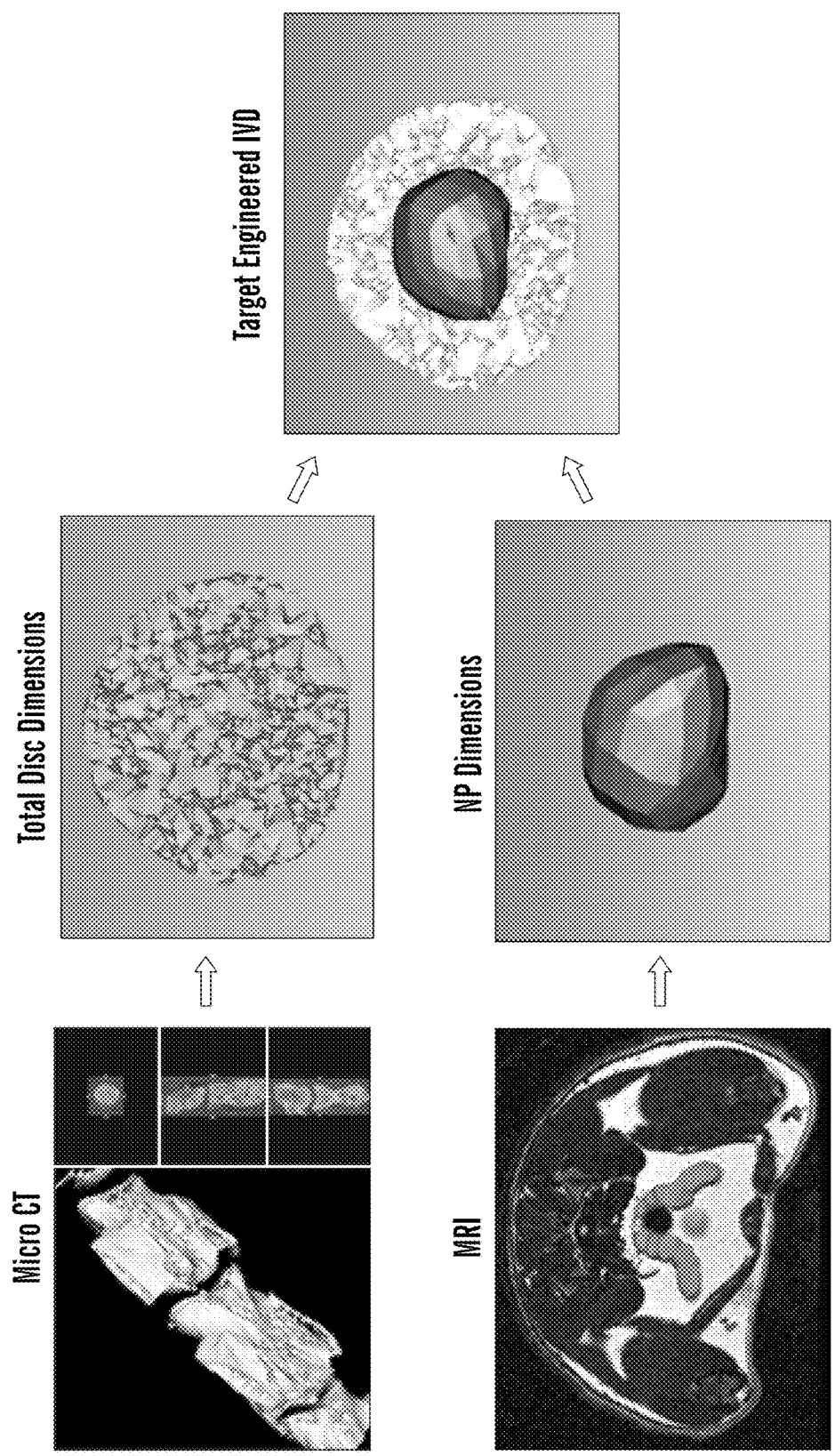
FIG. 26 is a schematic illustration showing the creation of an image-based model to produce total disc dimensions from μCT using the vertebral body surface and NP model from a T2 weighted MRI image. A combination of the MRI and μCT models produced the image-based model.
Figure 27:
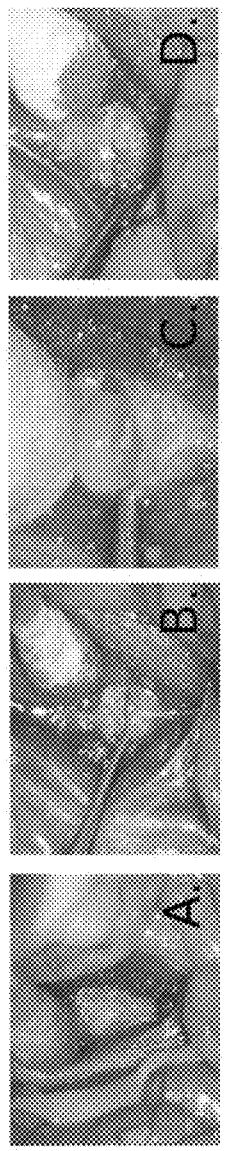
FIGS. 27A-D are photographs showing the surgical implantation of a tissue-engineered total disc replacement ("TE-TDR") (also referred to herein as a "tissue-engineered IVD") implant of the present invention into the L4/5 disc space.

Rat spine from L3-S1 was imaged using an MS-8 Micro-CT Scanner (GE Healthcare, London, Ontario, Canada) at an isotropic resolution of 17 µm. Scans were calibrated using an air, water, and mineral standard material (SB3, Gammex, RMI).

µCT data were visualized in Microview (GE Healthcare Inc., Princeton, N.J.) and converted to DICOM format. DICOM files were then imported into slicOmatic v4.3 (TomoVision, Montreal, Canada) where the bony surfaces of the vertebral bodies were manually segmented to obtain the overall shape and dimensions of the L4/L5 IVD (FIG. 26). In addition, the spacing between the vertebral bodies was obtained to determine the target thickness of the engineered IVD.

MRI data were imported in DICOM format and segmented manually using slicOmatic v4.3 to create point cloud images of the NP. Point cloud images were then converted to surface and solid models of the NP in Studio 4.0 (Geomagic Inc., Research Triangle Park, N.C.) (FIG. 26). As a result, the MRI generated NP data and the µET generated total disc measurements were combined to provide the target shape and dimensions of the IVD and respective AF and NP. In concordance with the collagen contraction method of creating engineered IVD (Bowles et al., "Self-Assembly of Aligned Tissue Engineered Annulus Fibrosus and IVD Composite via Collagen Gel Contraction," *Tissue Eng. Part A.* 16(4):1339-1348 (2010), which is hereby incorporated by reference in its entirety), the shape and dimensions of the NP were used to create injectable molds of the NP region of the disc (Ballyns et al., "Image-Guided Tissue Engineering of Anatomically Shaped Implants Via MRI and Micro-CT Using Injection Molding," *Tissue Eng. Part A* 14(7):1195-1202 (2008), which is hereby incorporated by reference in its entirety). Total disc dimensions, NP dimensions, and AF dimensions were measured on the AP and lateral plane for the native disc, the image-based model, and the engineered discs.

Isolation and preparation of AF and NP cells were conducted as described herein (Mizuno et al., "Tissue-Engineered Composites of Anulus Fibrosus and Nucleus Pulposus for Intervertebral Disc Replacement," *Spine* 29(12):1290-1297 (2004); discussion 1297-1298; Mizuno et al., "Biomechanical and Biochemical Characterization of Composite Tissue-Engineered Intervertebral Discs," *Biomaterials* 27(3):362-370 (2006); Bowles et al., "Self-Assembly of Aligned Tissue-engineered Annulus Fibrosus and IVD Composite via Collagen Gel Contraction," *Tissue Eng.* (2009), which are hereby incorporated by reference in their entirety). Four IVDs were removed from the lumbar region of an adult skeletally mature Fin/Dorset cross male sheep (Cornell University Sheep Program, Ithaca, N.Y.) and washed in phosphate buffered saline (PBS) solution (Dulbecco's Phosphate Buffered Saline, Gibco BRL, Grand Island, N.Y.). The AF and NP were subsequently separated by inspection and dissected into small pieces that were digested in 0.3% collagenase type II (Cannel Worthington Biochemicals, Malvern, Pa.), with the NP digested for six hours and the AF for nine hours. Digested tissue was filtered using a 100 µm nylon mesh (BD Biosciences, Bedford, Mass.) and centrifuged at 936×g for seven minutes. The cells were seeded at a density of 2500 cells/cm$^2$ in T150 flasks with Ham's F-12 media (Gibco BRL, Grand Island, N.Y.) supplemented with 10% fetal bovine serum (Gemini Bio Products, Sacramento, Calif.), 25 µg/ml ascorbic acid, 100 IU/ml penicillin, 100 µg/ml streptomycin, and 250 ng/ml amphotericin B. Cells were cultured to confluence at 37° C., 5% $CO_2$ atmosphere, and normoxia. Following culture, cells were removed from T-150 flasks with 0.05% trypsin (Gibco).

Example 14—IVD Construction, Implantation, and Analysis

Engineered IVD were constructed as described supra. Briefly, 3% (w/v) alginate seeded with ovine nucleus pulposus cells (25×10$^6$ cells/ml) was injection molded (FIG. 18) using molds derived from MRI and µCT images and alginate NP was placed in the center of a 24 well plate. Collagen type I gel solution (1 mg/ml) made from rat-tail tendon (Elsdale and Bard, "Collagen Substrata for Studies on Cell Behavior," *J. Cell Biol.* 54(3):626-637 (1972), which is hereby incorporated by reference in its entirety), seeded with ovine annulus fibrosus cells at a density of 1×10$^6$ cells/ml, was pipetted around the NP and allowed to gel at 37° C. using established protocols (Bowles et al., "Self-Assembly of Aligned Tissue-engineered Annulus Fibrosus and IVD Composite via Collagen Gel Contraction," *Tissue Eng.* (2009), which is hereby incorporated by reference in its entirety). Constructs were floated with F12 media supplemented with 10% FBS, 100 IU/ml penicillin, 100 µg/ml streptomycin, and 25 µg/ml ascorbic acid. Media was changed every 3 days and constructs were cultured for 2 weeks allowing the collagen gel region to contract around alginate NP to the dimensions derived from MRI and µCT data.

Figure 28:
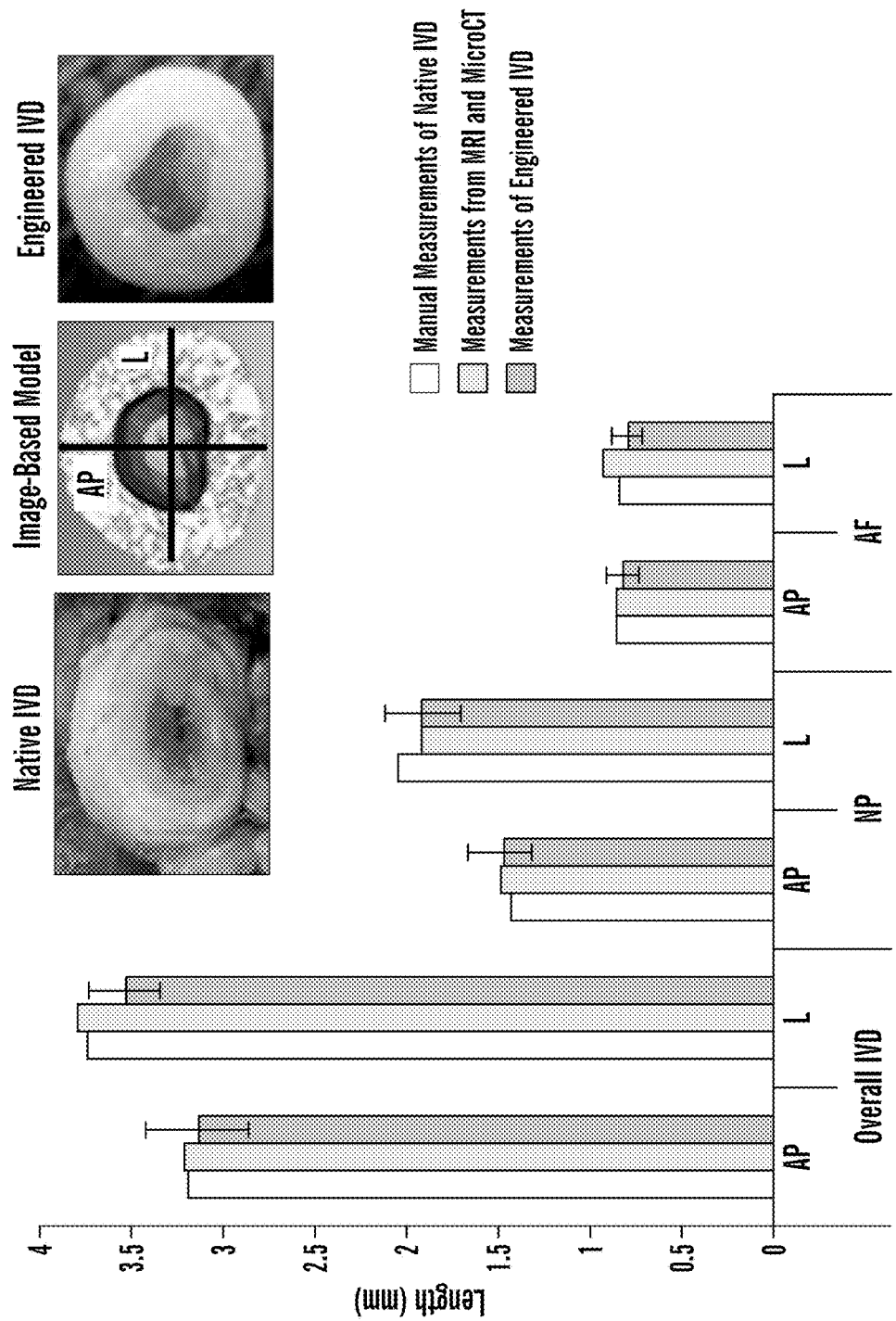
FIG. 28 is a graph showing comparisons of disc dimensions between the native IVD, image-based model, and TE-TDR according to one embodiment of the present invention (n=5). Measurement planes are indicated on the picture of the image-based model (the vertical line represents an anterior-posterior plane, the horizontal line represents a lateral plane).

After 2 weeks of in vitro culture, composite discs were implanted into the lumbar spine of athymic rats (n=5) (FIGS. 27A-D). All animal procedures were performed in accordance with the guidelines of the IACUC of the Hospital for Special Surgery, New York, N.Y. Rats were anesthetized using ketamine ('Ketaset'—100 mg/ml) 80-90 mg/kg, and xylazine ('Rompun'—20 mg/ml) 5 mg/kg, which were mixed together and administered intraperitoneally. If necessary, anesthesia was prolonged by administration of isoflurane via nose cone. A modified anterior approach was used to approach the lower lumbar spine (Rousseau et al., "Ventral Approach to the Lumbar Spine of the Sprague-Dawley Rat," *Lab Anim.* 33(6):43-45 (2004), which is hereby incorporated by reference in its entirety). A method was for the first time established to remove the native disc and to prepare the disc space for implant insertion. The vertebral column was exposed and the native IVD (L4/L5) removed. Upon removal, the L4 and L5 vertebral bodies were minimally retracted to allow the insertion of the engineered disc into the disc space (FIG. 28). The disc space was released to press-fit the implant in place and wound closure was performed in layers. An initial dose of 0.01-0.05 mg/kg buprenorphine (Buprenex) was administered intraoperatively or immediately postoperatively prior to anesthetic recovery. Buprenorphine treatments were performed for two days postoperatively.

Upon implantation, rats were maintained for 4 months with lateral and anterior-posterior x-ray images taken of the implanted disc space immediately prior to surgery, immediately after surgery, and at 1, 4, 8, 12, and 16 weeks to monitor disc height. At 4 months, rats were sacrificed and the motion segments explanted.

Spines and bone samples were cleaned of muscle and preserved in 10% phosphate buffered formalin or 4% paraformaldehyde in 0.05 M cacodylate buffer, pH 7.4. Samples were fixed at room temperature for 2 days using a rotator or rocker plate to agitate samples during fixation. Following an overnight running water rinse, samples were decalcified in 10% EDTA in 0.05 M Tris buffer, pH 7.4, until bone was soft and flexible. An overnight running water rinse was conducted in a VIP tissue processor to paraffin. Embedded samples were sectioned at 5 micron thickness and subsequently stained with safranin O for proteolycans, picrosirius red for collagen, and Hemotoxylin and eosin.

Analysis using immunohistochemistry was also conducted. Paraffin sections were dewaxed in xylene and rehydrated to water by a decreasing concentration of ethyl alcohol baths. The sections were treated with 3% hydrogen peroxide in PBS to reduce endogenous peroxidase activity in the tissues. A protein block was added to reduce the non-specific binding between antibody and tissue components. The antibody for collagen type II (Santa Cruz Biotechnology, Santa Cruz, Calif.) was used at a concentration of 250 µg protein per ml of solution. To enhance the type II collagen localization, the sections were treated with 1% hyaluronidase in PBS, pH 5.5 for 30 minutes at 37° C., prior to adding the antibody. After an overnight incubation in primary antibody at 4° C. in a humid chamber, the antibody was rinsed off with PBS, and treated with a biotinylated anti-mouse IgG followed by streptavidin reagents using the Vectastain ABC Kit (Vector Laboratories, Burlingame, Calif.) according to manufacturers instructions. The final reaction product was the brown deposit created by diaminobenzidine and hydrogen peroxide in the presence of the conjugated peroxidase.

The results show that a model of the native IVD was obtained from µCT and MRI imaging and provided the target dimensions for an engineered IVD to be implanted in the L4/L5 disc space. μCT provided the outer boundary and thickness of the IVD (FIG. 26), which measured an anterior-posterior width of 3.23 mm, a lateral width of 3.8 mm, and a thickness of 0.99 mm, while MRI data provided the dimensions for the NP region of the disc (FIG. 28), which measured an anterior posterior width of 1.50 mm and a lateral width of 1.93 mm. The combination of the NP (MRI) and total disc (μCT) data allowed for the dimensions of the AF to be determined with a measured AF width of 0.86 mm on the AP plane and 0.93 mm on the lateral plane. The dimensions of the image-derived model were within 10% of the manually measured dimensions of the native disc (FIG. 28). In addition, the engineered constructs differed by less than 7% from those of the native disc. Finally, the process had a high degree of reproducibility with the standard deviations ranging from 78-278 μm (FIG. 28). These standard deviations were within 11.8% of the mean in all measurements.

Upon implantation, none of the rats showed any signs of neurological deficit due to the surgery and implantation. Radiographs indicated the disc space was fully or partially maintained in three of five animals at the implanted level (FIGS. 29A-C) after 4 months. Two of the discs failed rapidly with a complete collapse of the disc space occurring by 4 weeks with one disc losing disc space constantly over the 4 months to 50% of the original disc space. In each of the animals with collapsed disc space the posterior longitudinal ligament had been removed during surgery.

Histologically, the 3 samples that maintained disc height produced tissue with composition reminiscent of native IVD (FIG. 30), while those that resulted in a collapsed disc space produced a fusion between the vertebral bodies. Implanted tissues were generally located anteriorly in the disc space with significant staining observed for both proteoglycans and collagen in the implanted discs at 4 months (FIG. 30, S1-2, P1-2). Collagen II was seen distributed throughout the implanted disc at 4 months by immunohistochemistry. In addition, proper localization of proteogylcan and collagen was observed in one of the maintained disc spaces (FIGS. 31A and 31C). The NP region contained intense proteoglycan staining compared to the AF region of the implant while the AF region showed increased staining for collagen compared to the NP region. Good integration was observed between the AF and NP regions of the TE-TDR (FIGS. 31A and 31C) and between the TE-TDR and remnant native IVD (FIG. 30, 51, P1). Furthermore, picrosirius red staining and polarized light images indicated that the AF region contained collagen organization at 4 months (FIGS. 31A and 31B). Finally, in each of the animals that successfully maintained disc space, good integration was observed between the implanted disc and the vertebral bone (FIG. 31D).

Example 15—Clinically Relevant Imaging Data was Effectively Used to Design Implants to a High Degree of Geometric Accuracy The aim of this work was to use MRI and μCT to design a natively sized tissue-engineered IVD and study the performance of those implants in the rat lumbar spine. This research provides a method of using clinically relevant imaging data to design implants to a high degree of geometric accuracy. Initial characterization of these implants showed that the implanted TE-TDR was capable of maintaining disc height, integrating with the vertebral bodies, and developing in the native disc space.

Recently, a number of studies have focused on creating composite engineered IVD implants containing both an AF and NP. A major concern is producing a construct that is the correct size and shape for the targeted disc space. One possible solution is to make generalized measurements and have a number of sizes available during implantation to find the correct fit; however, this may not be practical in tissue engineering due to the cellular cost of producing multiple sized constructs. For this reason, this work focused on using clinically applicable imaging modalities to determine the necessary disc dimensions for implantation.

Using μCT and MRI, a model of the desired IVD was successfully produced from the native rat disc (FIG. 26). In addition, when comparing measurements obtained from the actual native disc and that obtained from imaging, the technique was shown to be quite accurate even for the relatively small rat discs (FIGS. 27A-D) with the maximum deviations between measurements being 99 μm. While used here for the rat, this technique could be employed clinically to design tissue-engineered IVDs for larger animals or humans. It should be noted, however, one would not want to copy a degenerated NP in a tissue-engineered implant. A more likely clinical scenario would be to obtain the disc space boundaries using CT and design the NP within those overall boundaries using established values for the NP relative to the disc or obtain them from an adjacent healthy disc.

This study produced IVD composites using the collagen contraction method, which resulted in an AF region with circumferentially aligned collagen fibrils and a cell-seeded alginate NP. By controlling the NP shape and dimensions through injection molding (FIG. 18), an accurate alginate NP was created (FIG. 28) compared to the native NP and image-based model; however, the thickness of the gel was purposely oversized. The degree of accuracy and repeatability is consistent with previous work when using alginate injection molding to produce tympanic membrane patches (Hat et al., "Fabrication of Tissue Engineered Tympanic Membrane Patches Using computer-Aided Design and Injection Molding," Laryngoscope 114(7):1290-1295 (2004), which is hereby incorporated by reference in its entirety). The oversized implant was designed to be press fit into the disc space and combat slippage of the engineered disc from the disc space before integration. In addition, this allowed for the alginate and collagen material to be flush with the vertebral ends and promote integration between the native and engineered tissue. Once the NP was created, the collagen gel AF was contracted around the alginate NP to the AF dimensions provided by the image-based model. Upon completion, this technique resulted in engineered IVDs that were similar in dimension to that of the native IVD and image-based measurements (FIG. 28).

Figure 29:
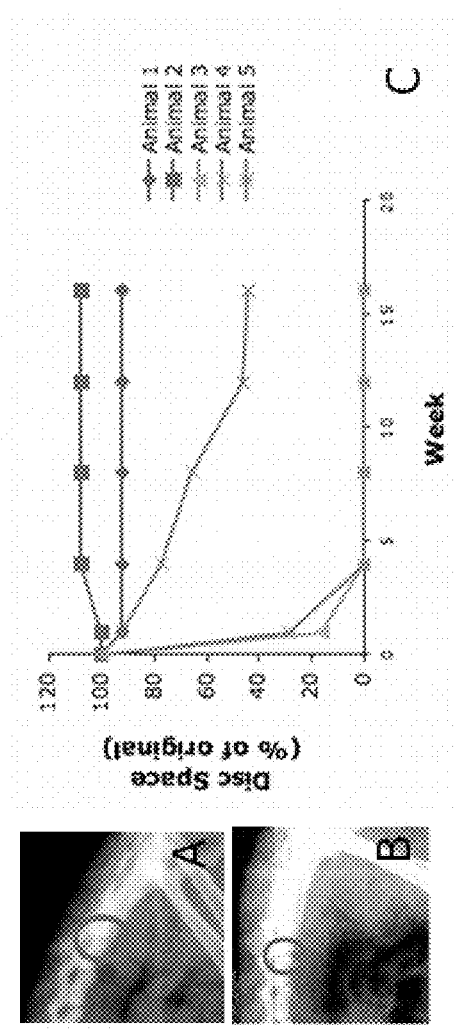
FIGS. 29A-C show X-ray images of disc space immediately following surgery (FIG. 29A) and 4 months following implantation (FIG. 29B). Disc height measurements were obtained over 4 months from 5 implanted animals (FIG. 29C).

Upon implantation into the rat L4/L5 disc space, three of five rats showed full or partial disc height maintenance at the implanted level (FIG. 29C). The failure of two of the discs to maintain disc height was seen in animals in which the posterior supporting tissue, including the posterior lateral ligament ("PLL"), had been more aggressively removed. Removal of the supporting tissue provided a possible mechanism for the destabilization of the spine and collapse of the disc space. The maintenance of disc height in the remaining animals shows promise for this type of implant. This indicates that, under the proper conditions, a contracted collagen/alginate implant can function in the basic capacity of maintaining disc height despite a relatively low stiffness of these discs when compared to the modulus of a native disc. Current work has focused on the replication of the native mechanical properties as a key outcome variable in in vitro IVD tissue engineering (Mizuno et al., "Biomechanical and Biochemical Characterization of Composite Tissue-Engineered Intervertebral Discs," *Biomaterials* 27(3):362-370 (2006); Nerurkar et al., "Nanofibrous Biologic Laminates Replicate the Form and Function of the Annulus Fibrosus," *Nature mater.* 8(12):986-992 (2009), which are hereby incorporated by reference in their entirety). However, the data presented here indicates that it may not be necessary for clinically viable TE-TDR to fully replicate the native mechanical properties before implantation. As a result, this may allow for greater focus to be placed on other properties of the TE-TDR, such as permeability, that would encourage nutrient transport and aid tissue formation and integration within the nutrient limited disc space.

In addition to the maintenance of disc height, the successful implants showed patterns of proteoglycan and collagen staining that were similar to native IVD (FIG. 30). Significant proteoglycan and collagen staining was observed in the implanted tissue at 4 months (FIG. 30, S1-2, P1-2, C1a-b) indicating a cartilaginous tissue being formed by the constructs within the disc space. Furthermore, in one of the successful constructs the NP region showed increased proteoglycan staining and lower collagen staining in comparison to the AF region (FIGS. 31A and 31C). Polarized light indicated that the collagen organization in the AF was maintained after 4 months. These findings indicate that these constructs are quite capable of producing cartilaginous tissues in the disc space environment and promoting IVD like qualities in their development.

For total tissue-engineered discs to succeed in the disc space, there needs to be integration of the implant with the vertebral bodies. Without this occurrence it is likely the disc will not remain in the disc space over time. This study observed very good integration between the implant and vertebral bodies (FIG. 31D) and remnant IVD (FIG. 30, S1, P1) at 4 months. This demonstrates that given the proper conditions total tissue-engineered discs can integrate with their environment and create a mechanically functioning motion segment. Furthermore, not to be overlooked is the successful integration of the TE-TDR materials with the remnant native IVD. The integration indicates that these materials can be used in annular repair following discectomy and allow for new tissue to be developed in the annular defect and prevent rehermiation following surgery.

Overall, this work provides both a method of creating anatomically shaped IVDs with clinically relevant imaging modalities, as well as providing the first insight into how engineered discs perform in the native disc space. Specifically, anatomically shaped engineered IVDs were seen maintaining disc height in a significant portion of cases, developing cartilaginous like tissue in the disc space, and integrating with the native bone. These results show that TE-TDRs can be developed in a manner that would be clinically applicable.

Example 16—Transplantation of Composite Tissue-Engineered Intervertebral Discs to Restore Function to the Rat Spine To investigate the in vivo function of the contracted collagen gel composite discs to survive, integrate, and restore disc function to the rat spine, the following experiments were performed.

Composite-engineered IVD discs were created by contracting collagen gels around an alginate NP thus creating circumferentially aligned collagen fibrils in the engineered AF, as described supra. Rat lumbar disc dimensions were obtained from µCT images and direct measurements of the rat lumber IVD. Dimensions were then used to create an injection mold of the rat NP. 3% (w/v) alginate seeded with ovine nucleus pulposus cells ($25 \times 10^6$ cells/ml) was injection molded and alginate NP was placed in the center of a 24 well plate. Collagen type I gel solution (1 mg/ml) made from rat tail tendon, seeded with ovine annulus fibrosus cells ($1 \times 10^6$ cells/ml), was pipetted around the NP and allowed to gel at 37° C. Constructs were floated with F12 media supplemented with 10% FBS, 100 IU/ml penicillin, 100 µg/ml streptomycin, and 25 µg/ml ascorbic acid. Media was changed every 3 days and constructs cultured for 2 weeks allowing the collagen gel region to contract around alginate NP.

After 2 weeks of in vitro culture, composite discs were implanted into the lumbar spine of athymic rats (n=5). All animal procedures were performed in accordance with the guidelines of the IACUC. Using an anterior approach the vertebral column was exposed and the native IVD (L4/L5) removed. Upon removal, the L4 and L5 vertebral bodies were minimally retracted to allow the insertion of the engineered disc into the disc space (FIGS. 23A-D).

Rats were maintained for 3 months with x-ray images taken of the implanted disc space immediately prior to surgery, immediately after surgery and at 1, 4, 8, and 12 weeks to monitor disc height. At 3 months, rats were sacrificed and the tissue explanted for gross morphology inspection, histology, and immunohistochemistry (IHC).

Figure 24:
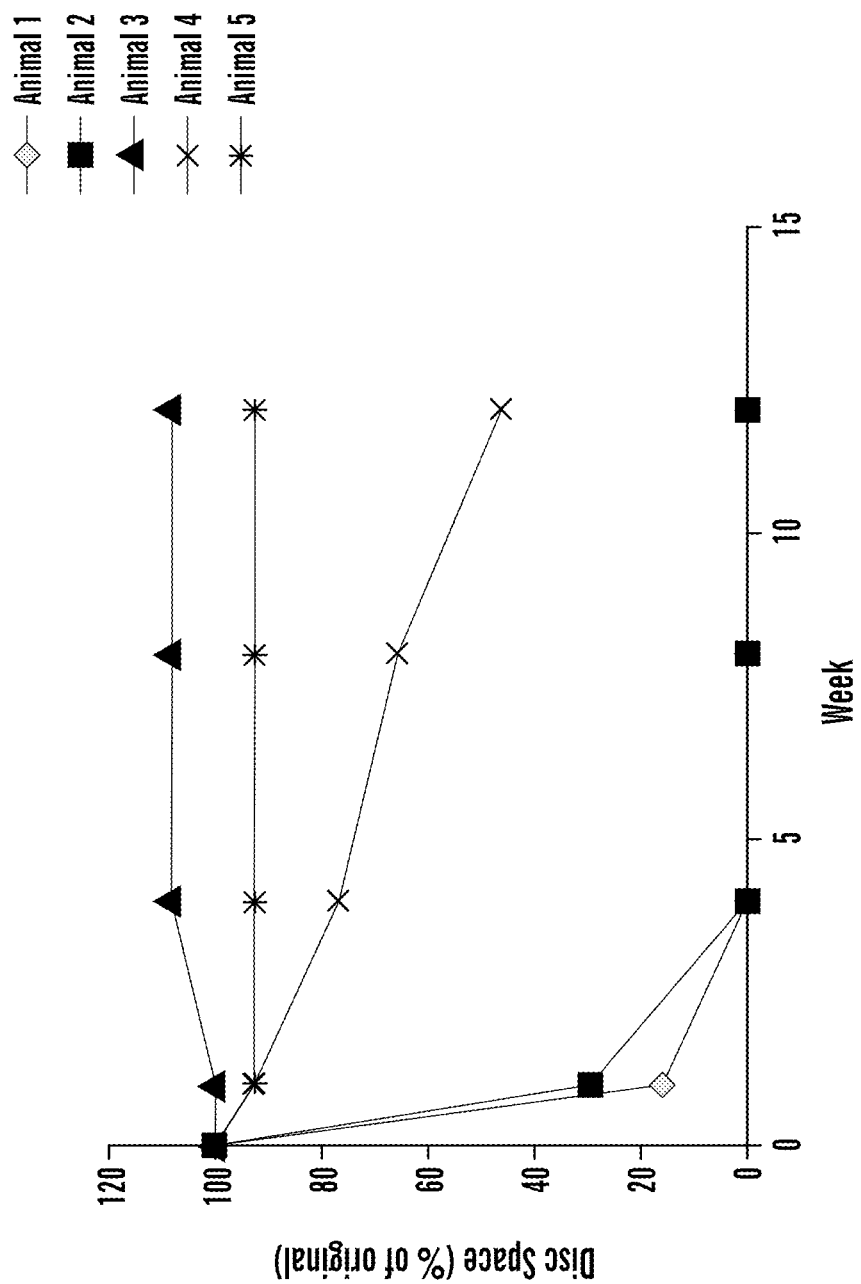
FIG. 24 is a graph showing disc space of a tissue-engineered IVD of the present invention represented as a percentage of original disc space over 3 months.
Figure 25:
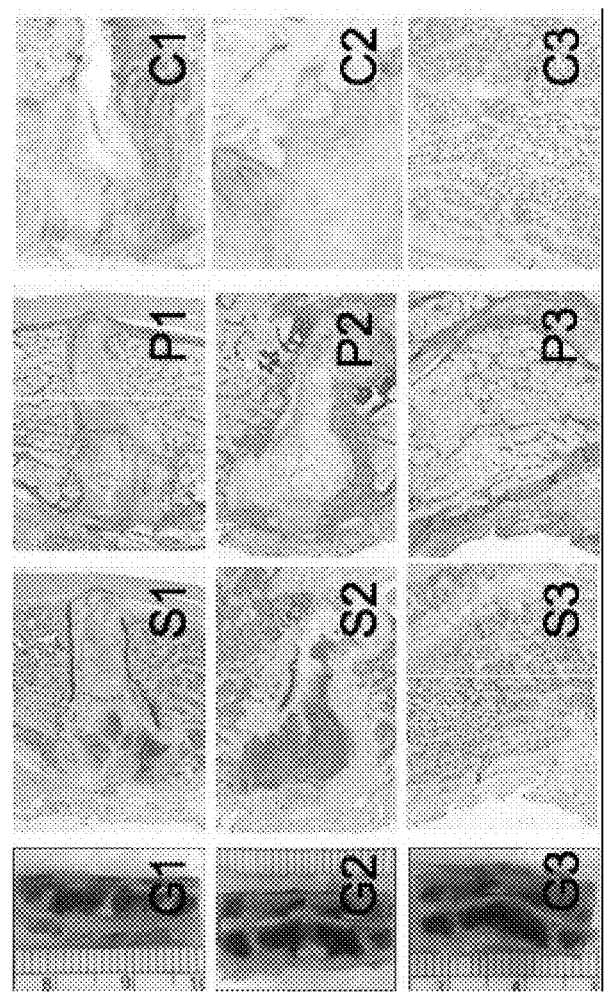
FIG. 25 presents photographs showing gross sections (G1-3), Safranin-O (S1-3), picrosirius red (P1-3), and collagen II immunohistochemistry ("IHC") (C1-3) histology of tissue-engineered IVDs according to the present invention. G1-2, S1-2, P1-2, and C1-2 show tissue development in IVDs that maintained disc space. S3, P3, and C3 show fused vertebral bodies at the site of the implanted disc.

Upon implantation of engineered IVD constructs, all animals returned to normal activity levels and showed no signs of neurological deficit. Furthermore, engineered discs fully or partially maintained disc space in 3 of 5 cases (FIG. 24). Upon inspection, it was discovered that in the 3 cases that failed to maintain full disc height, the posterior longitudinal ligament had been severed during surgery. Histology showed the development of disc like tissue in the disc space containing both proteoglycans and collagen (FIG. 25). In addition, engineered tissue showed good integration with the adjacent bone and remaining native IVD tissue. Discs were pushed towards the anterior side of the disc space.

This study demonstrates the ability of a composite tissue-engineered IVD to survive, integrate, and restore function to the rat spine. Overall, the study showed that engineered IVD tissues can be implanted and maintained in the IVD disc space (FIG. 25), producing a tissue that was both IVD like in its ECM composition (S1-2, P1-2, C1) but also integrated with the bone (C2) and remaining native IVD tissue (C1).

It was observed that the discs were found toward the anterior region of the disc space indicating that the discs may have had difficulty remaining in the disc space (S1-2). Thus, anchoring or containment strategies may be used with implanted engineered discs. In addition, the discovery that the PLL had been severed in all 3 of the failed discs highlights the need for a stable environment to be present for the implanted tissue to be successful and integrate with the native tissues. Taken as a whole, this work shows that engineered tissues can form IVD like tissue and integrate successfully with bone in the lumbar disc space.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of fabricating a tissue-engineered intervertebral disc (IVD) suitable for total disc replacement in a mammal, said method comprising:
   providing a first gel comprising a first population of living cells that secrete a hydrophilic protein;
   forming the first gel into a predetermined shape and size;
   providing a second different gel comprising a second different population of living cells and collagen;
   contacting the formed first gel with the second gel at a region that extends circumferentially around the first gel; and
   storing the first and second gels under conditions effective for the collagen in the second gel to align circumferentially around the first gel by self-assembly of collagen due to cell-mediated gel contraction in the second gel, wherein the first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

2. The method according to claim 1, wherein the first gel is an alginate gel comprising about 0.5% to about 10% (w/v) alginate.

3. The method according to claim 1, wherein the first population of cells is present in the first gel at a concentration of about $1 \times 10^6$ to about $50 \times 10^6$ cells/ml.

4. The method according to claim 1, wherein the first population of cells secrete a proteoglycan.

5. The method according to claim 1, wherein the first populations of cells comprises nucleus pulposus cells.

6. The method according to claim 1, wherein the first gel further comprises type II collagen.

7. The method according to claim 1, wherein the nucleus pulposus has an isotropic structure.

8. The method according to claim 1, wherein the second population of cells comprises annulus fibrosus cells.

9. The method according to claim 1, wherein the second population of cells are present in the second gel at a concentration of about $0.1\text{-}5.0 \times 10^7$ cells/ml.

10. The method according to claim 1, wherein the second gel comprises collagen at a concentration of about 1 mg/ml to about 30 mg/ml.

11. The method according to claim 1, wherein the annulus fibrosus has an anisotropic structure.

12. The method according to claim 1, wherein the IVD is permeable to allow nutrient transport to developing tissue.

13. The method according to claim 1 further comprising:
   cross-linking the first gel.

14. The method according to claim 1, the second gel is formed at a temperature of about 25° C. to about 37° C.

15. The method according to claim 1, wherein said storing is carried out for about 3 to about 28 days.

16. The method according to claim 1, wherein said forming is carried out by injection molding or by cutting samples from a sheet.

17. A method of fabricating a tissue-engineered intervertebral disc (IVD) suitable for total disc replacement in a mammal, said method comprising:
   providing a first gel comprising a first population of living cells that secrete a hydrophilic protein;
   providing a second different gel comprising a second different population of living cells and collagen;
   forming the second gel around a central mandrel structure;
   storing the second gel under conditions effective for the collagen in the second gel to align circumferentially around the central mandrel by self-assembly of collagen due to cell-mediated gel contraction in the second gel;
   replacing the central mandrel with the first gel, wherein the first gel forms a nucleus pulposus structure and the second gel forms an annulus fibrosus structure surrounding and in contact with the nucleus pulposus structure, thereby fabricating a tissue-engineered IVD suitable for total disc replacement in a mammal.

18. The method according to claim 17, further comprising:
   forming the first gel into a predetermined shape and size.

19. The method according to claim 17, wherein the mandrel comprises plastic or metal.

20. The method according to claim 17, wherein said forming is carried out by injection molding or by cutting samples from a sheet.

* * * * *